(12) United States Patent
Parker et al.

(10) Patent No.: US 11,413,460 B2
(45) Date of Patent: Aug. 16, 2022

(54) METHOD AND APPARATUS FOR APPLICATION OF A NEURAL STIMULUS

(71) Applicant: Saluda Medical Pty Ltd, Artarmon (AU)

(72) Inventors: John Louis Parker, Artarmon (AU); James Hamilton Wah, Artarmon (AU); Dean Michael Karantonis, Artarmon (AU); Milan Obradovic, Artarmon (AU); Robert Bruce Gorman, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 0 days.

(21) Appl. No.: 17/693,577

(22) Filed: Mar. 14, 2022

(65) Prior Publication Data

US 2022/0193416 A1    Jun. 23, 2022

Related U.S. Application Data

(63) Continuation of application No. 17/576,060, filed on Jan. 14, 2022, which is a continuation of application
(Continued)

(30) Foreign Application Priority Data

May 13, 2011  (AU) .................... 2011901828
May 13, 2011  (AU) .................... 2011901829

(51) Int. Cl.
*A61N 1/36*      (2006.01)
*A61N 1/05*      (2006.01)

(52) U.S. Cl.
CPC ....... *A61N 1/36139* (2013.01); *A61N 1/0551* (2013.01); *A61N 1/36071* (2013.01); *A61N 1/36167* (2013.01)

(58) Field of Classification Search
None
See application file for complete search history.

(56) References Cited

U.S. PATENT DOCUMENTS

| 3,724,467 A | 4/1973 | Avery et al. |
| 3,736,434 A | 5/1973 | Darrow |
(Continued)

FOREIGN PATENT DOCUMENTS

| AU | 2013277009 | 1/2016 |
| CN | 103648583 | 3/2014 |
(Continued)

OTHER PUBLICATIONS

Extended European Search Report in European Appln No. 19793420.1, dated Dec. 17, 2021, 9 pages.
(Continued)

*Primary Examiner* — Ankit D Tejani
(74) *Attorney, Agent, or Firm* — Fish & Richardson P.C.

(57) ABSTRACT

A method of applying a neural stimulus with an implanted electrode array involves applying a sequence of stimuli configured to yield a therapeutic effect while suppressing psychophysical side effects. The stimuli sequence is configured such that a first stimulus recruits a portion of the fibre population, and a second stimulus is delivered within the refractory period following the first stimulus and the second stimulus being configured to recruit a further portion of the fibre population. Using an electrode array and suitable relative timing of the stimuli, ascending or descending volleys of evoked responses can be selectively synchronised or desynchronised to give directional control over responses evoked.

10 Claims, 14 Drawing Sheets

Related U.S. Application Data

No. 17/514,650, filed on Oct. 29, 2021, which is a continuation of application No. 17/501,823, filed on Oct. 14, 2021, which is a continuation of application No. 17/489,710, filed on Sep. 29, 2021, which is a continuation of application No. 17/478,793, filed on Sep. 17, 2021, which is a continuation of application No. 17/031,749, filed on Sep. 24, 2020, which is a continuation of application No. 15/846,069, filed on Dec. 18, 2017, now abandoned, which is a continuation of application No. 14/844,929, filed on Sep. 3, 2015, now Pat. No. 9,872,990, which is a continuation of application No. 14/117,586, filed as application No. PCT/AU2012/000515 on May 11, 2012, now Pat. No. 9,155,892.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford |
| 4,418,695 A | 12/1983 | Buffet |
| 4,474,186 A | 10/1984 | Ledley |
| 4,628,934 A | 12/1986 | Pohndorf et al. |
| 4,807,643 A | 2/1989 | Rosier et al. |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | Dilorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,538,541 B2 | 9/2013 | Milojevic et al. |
| 8,588,929 B2 | 11/2013 | Davis et al. |
| 8,620,459 B2 | 12/2013 | Gibson et al. |
| 8,655,002 B2 | 2/2014 | Parker |
| 8,670,830 B2 | 3/2014 | Carlson et al. |
| 8,886,323 B2 | 11/2014 | Wu et al. |
| 8,945,216 B2 | 2/2015 | Parker et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,566,439 B2 | 2/2017 | Single et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0116978 A1 | 6/2004 | Bradley |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Fassio |
| 2005/0017190 A1 | 1/2005 | Eversmann et al. |
| 2005/0021104 A1 | 1/2005 | Dilorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |

(56) References Cited

U.S. PATENT DOCUMENTS

| | | |
|---|---|---|
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0216064 A1 | 9/2005 | Heruth et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Grber et al. |
| 2011/0077712 A1 | 3/2011 | Killian |
| 2011/0087085 A1 | 4/2011 | Tsampazi et al. |
| 2011/0093042 A1 | 4/2011 | Torgerson et al. |
| 2011/0106100 A1 | 5/2011 | Bischoff |
| 2011/0130802 A1 | 6/2011 | Libbus et al. |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0268043 A1 | 10/2013 | Tasche et al. |
| 2013/0289661 A1 | 10/2013 | Griffith et al. |
| 2013/0289683 A1 | 10/2013 | Parker et al. |
| 2014/0046407 A1 | 2/2014 | Ben-Ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0051637 A1 | 2/2015 | Osorio |
| 2015/0126839 A1 | 5/2015 | Li et al. |
| 2015/0148869 A1 | 5/2015 | Dorvall et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker et al. |
| 2016/0082265 A1 | 3/2016 | Moffitt et al. |
| 2016/0082268 A1 | 3/2016 | Hershey et al. |
| 2016/0101289 A1 | 4/2016 | Stolen et al. |

(56) References Cited

U.S. PATENT DOCUMENTS

| | | | |
|---|---|---|---|
| 2016/0106980 A1 | 4/2016 | Surth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0016091 A1 | 1/2021 | Parker et al. |
| 2021/0121696 A1 | 4/2021 | Parker et al. |
| 2021/0162214 A1 | 6/2021 | Parker |
| 2022/0023634 A1 | 1/2022 | Parker et al. |
| 2022/0023636 A1 | 1/2022 | Parker et al. |
| 2022/0032066 A1 | 2/2022 | Parker et al. |
| 2022/0047871 A1 | 2/2022 | Parker et al. |

FOREIGN PATENT DOCUMENTS

| | | |
|---|---|---|
| CN | 103654762 | 3/2014 |
| CN | 103842022 | 6/2014 |
| CN | 104411360 | 3/2015 |
| EP | 219084 | 4/1987 |
| EP | 1244496 | 10/2002 |
| EP | 0998958 | 8/2005 |
| EP | 2019716 | 11/2007 |
| EP | 2243510 | 10/2010 |
| EP | 2443995 | 4/2012 |
| EP | 2520327 | 11/2012 |
| EP | 2707095 | 3/2014 |
| EP | 3229893 | 10/2017 |
| JP | 2006504494 | 2/2006 |
| JP | 2009512505 | 3/2009 |
| JP | 2012524629 | 10/2012 |
| JP | 2013500779 | 1/2013 |
| JP | 2013527784 | 7/2013 |
| JP | 2013536044 | 9/2013 |
| JP | 2014522261 | 9/2014 |
| JP | 2014523261 | 9/2014 |
| WO | WO 1983003191 | 9/1983 |
| WO | WO 1993001863 | 2/1993 |
| WO | WO 1996012383 | 4/1996 |
| WO | WO 2000002623 | 1/2000 |
| WO | WO 2002036003 | 11/2001 |
| WO | WO 2002038031 | 5/2002 |
| WO | WO 2002049500 | 6/2002 |
| WO | WO 2002082982 | 10/2002 |
| WO | WO 2003028521 | 4/2003 |
| WO | WO 2003043690 | 5/2003 |
| WO | WO 2003103484 | 12/2003 |
| WO | WO 2004021885 | 3/2004 |
| WO | WO 2004103455 | 12/2004 |
| WO | WO 2005032656 | 4/2005 |
| WO | WO 2005105202 | 11/2005 |
| WO | WO 2005122887 | 12/2005 |
| WO | WO 2006091636 | 8/2006 |
| WO | WO 2007050657 | 5/2007 |
| WO | WO 2007064936 | 6/2007 |
| WO | WO 2007127926 | 11/2007 |
| WO | WO 2007130170 | 11/2007 |
| WO | WO 2008004204 | 1/2008 |
| WO | WO 2008049199 | 5/2008 |
| WO | WO 2009002072 | 12/2008 |
| WO | WO 2009002579 | 12/2008 |
| WO | WO 2009010870 | 1/2009 |
| WO | WO 2009130515 | 10/2009 |
| WO | WO 2009146427 | 12/2009 |
| WO | WO 2010013170 | 2/2010 |
| WO | WO 2010044989 | 4/2010 |
| WO | WO 2010051392 | 5/2010 |
| WO | WO 2010051406 | 5/2010 |
| WO | WO 2010057046 | 5/2010 |
| WO | WO 2010124139 | 10/2010 |
| WO | WO 2010138915 | 12/2010 |
| WO | WO 2011011327 | 1/2011 |
| WO | WO 2011014570 | 2/2011 |
| WO | WO 2011017778 | 2/2011 |
| WO | WO 2011066477 | 6/2011 |
| WO | WO 2011066478 | 6/2011 |
| WO | WO 2011112843 | 9/2011 |
| WO | WO 2011119251 | 9/2011 |
| WO | WO 2011159545 | 12/2011 |
| WO | WO 2012027252 | 3/2012 |
| WO | WO 2012027791 | 3/2012 |
| WO | WO 2012155183 | 11/2012 |
| WO | WO 2012155184 | 11/2012 |
| WO | WO 2012155185 | 11/2012 |
| WO | WO 2012155187 | 11/2012 |
| WO | WO 2012155188 | 11/2012 |
| WO | WO 2012155189 | 11/2012 |
| WO | WO 2012155190 | 11/2012 |
| WO | WO 2012162349 | 11/2012 |
| WO | WO 2013063111 | 5/2013 |
| WO | WO 2013075171 | 5/2013 |
| WO | WO 2014071445 | 5/2014 |
| WO | WO 2014071446 | 5/2014 |
| WO | WO 2014143577 | 9/2014 |
| WO | WO 2014150001 | 9/2014 |
| WO | WO 2015070281 | 5/2015 |
| WO | WO 2015074121 | 5/2015 |
| WO | WO 2015109239 | 7/2015 |
| WO | WO 2015143509 | 10/2015 |
| WO | WO 2015168735 | 11/2015 |
| WO | WO 2016011512 | 1/2016 |
| WO | WO 2016048974 | 3/2016 |
| WO | WO 2016059556 | 4/2016 |
| WO | WO 2016077882 | 5/2016 |
| WO | WO 2016090420 | 6/2016 |
| WO | WO 2016090436 | 6/2016 |
| WO | WO 2016115596 | 7/2016 |
| WO | WO 2016161484 | 10/2016 |
| WO | WO 2016168798 | 10/2016 |
| WO | WO 2016191807 | 12/2016 |
| WO | WO 2016191808 | 12/2016 |
| WO | WO 2016191815 | 12/2016 |
| WO | WO 2017053504 | 3/2017 |
| WO | WO 2017173493 | 10/2017 |
| WO | WO 2017210352 | 12/2017 |
| WO | WO 2017219096 | 12/2017 |
| WO | WO 2018119220 | 6/2018 |
| WO | WO 2018160992 | 9/2018 |
| WO | WO 2019204884 | 10/2019 |

(56) References Cited

FOREIGN PATENT DOCUMENTS

| WO | WO 2019231796 | 12/2019 |
|---|---|---|
| WO | WO 2020082118 | 4/2020 |
| WO | WO 2020082126 | 4/2020 |
| WO | WO 2020087123 | 4/2020 |
| WO | WO 2020082128 | 5/2020 |
| WO | WO 2020087135 | 5/2020 |
| WO | WO 202012413 5 | 6/2020 |

OTHER PUBLICATIONS

"Advanced Pain Therapy using Neurostimulation for Chronic Pain", Medtronic RestoreSensor clinical trial paper,Clinical summary, Nov. 2011, p. 32.
"Battelle Neurotechnology—Moving Beyond The Limits In Neurotechnology", Battelle, www.battelle.org, May 2014, pp. 1-2.
"Evoke 12C Percutaneous Leads", Saluda Medical, specifications available in the "Evoke Surgical Guide", version 6, http://www.saludamedical.com/manuals/, retrieved May 2017.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Abra Rd et al., "A time-frequency blindsignal separation methodapplicable to underdetermined mixtures of dependent sources", Signal Processing 85 (2005) 1389-1403.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Australian Examination Report for Application No. 2019283936, dated Apr. 1, 2021, 7 pages.
Bahm Er et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahm Er et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1 : pp. 200-205.
Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatiy, vol. 50, 1987, 443-446.

Bratta et al., "Orderly Stimulation of Skeletal Muscle Motor Units with Tri polar Nerve Cuff Electrode", IEEE Transactions on Biomedical Engineering, vol. 36, No. 8, 1989.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE, vol. 6, IEEE, 1992, pp. 2600-2601.
Casey et al., "Separation of Mixed Audio Sources by Independent Subspace Analysis", Mitsubishi Electric Research Laboratories (2001).
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi: 10.1111/j. 1526-4637. 2009. 00632 .X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13,No. 2, pp. 161-163.
Dawson, G. D., "The relative excitability and conduction velocity of sensory and motor nerve fibres in man", Journal of Physiology, 1956, vol. 131 (2), pp. 436-451.
De Ri Oder et al., "Burst Spinal Cord Stimulation toward Paresthesia-Free Pain Suppression", Nuerosurgeiy-online.com, May 2010, vol. 66, No. 8, pp. 986-990.
Delgado et al., "Measurement and interpretation of electrokinetic phenomena", Pure Appl. Chem., 2005, vol. 77, No. 10, pp. 1753-1805.
Devergnas et al., A, "Cortical potentials evoked by deep brain stimulation in the subthalamic area", Frontiers in System Neuroscience, May 13, 2011, vol. 5, Article 30, 2011, doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N et al., "Measurement of the electrically evoked compound action potential via a neural response telemetiy system", Ann. Otol. Rhinol. Laryngol., vol. 111, No. 5, May 2002, pp. 407-414.
Doi Ron et al., "Persistent Na+ Current Modifies Burst Discharge By Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 9 Pgs.
Extended European Search Report for European Application No. 14861553.7, Search completed Jun. 8, 2017, dated Jun. 19, 2017, 8 Pgs.

(56) References Cited

OTHER PUBLICATIONS

Extended European Search Report for European Application No. 14863597.2, Search completed Jun. 6, 2017, dated Jun. 13, 2017, 9 Pgs.
Extended European Search Report for European Application No. 15768956.3, Search completed Oct. 3, 2017, dated Oct. 10, 2017, 8 Pgs.
Extended European Search Report for European Application No. 15789515.2, Search completed Dec. 4, 2017, dated Jan. 30, 2018, 7 pgs.
Extended European Search Report for European Application No. 16739680.3, Search completed Jun. 1, 2018, dated Jun. 12, 2018, 9 Pgs.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
Extended European Search Report for European Application No. 13853514.1, Search completed Jun. 8, 2016, dated Jun. 15, 2016, 7 Pgs.
Extended European Search Report in European Appln No. 18910394.8, dated Oct. 15, 2021, 8 pages.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientificWorldJournal, (2007) 7, pp. 144-160.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Franke et al., Felix, "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs., http://www.jneuroengrehab.com/content/10/1/2.
George et al., "Vagus nerve stimulation: a new tool forbrain research and therapy", Biological Psychiatiy 47, No. 4, Feb. 15, 2000, pp. 287-295.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.

Gorman et al., "ECAP Mapping of the Spinal Cord: Influence of Electrode Position on A13 Recruitment", (2012)., In 16th Annual Meeting. Presented at the North American Neuromodulation Society, Las Vegas, NV, 2 pgs.
Gorman et al., "Neural Recordings For Feedback Control of Spinal Cord Stimulation: Reduction of Paresthesia Variability.", 2013, In International Neuromodulation Society 11th World Congress, presented at the International Neuromodulation Society 11th World Congress, Berlin, Germany, 2 pgs.
Hallstrom et al., "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.
Harper et al., A. A., "Conduction Velocity is Related to Morphological Cell Type in Rat Dorsal Root Ganglion Neurones", J. Physiol, (1985), vol. 359, pp. 31-46.
He et al., "Perception threshold and electrode position for spinal cord stimulation", Pain, vol. 59, (1994), pp. 55-63.
Herreras, "Local Field Potentials: Myths and Misunderstandings", Frontiers in Neural Circuits, Dec. 15, 2 016, vol. 10, Article 1101, 16 pgs., doi:10.3389/fncir.2016.00101.
Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.
Holsheimer et al., "Significance of the Spinal Cord Position in Spinal Cord Stimulation", Acta Neurochir(1995) [Suppl] 64, pp. 119-124.
Holsheimer et al., "Spinal Geometry and Paresthesia Coverage in Spinal Cord Stimulation", Neuromodulation, 1998, vol. 1, No. 3, pp. 129-136.
Howell et al., "Evaluation of Intradural Stimulation Efficiency and Selectivity in a Computational Model of Spinal Cord Stimulation", PLOS ONE, DOI:10.1371/journal.pone.0114938, Dec. 23, 2014.
Huff, Terry B. et al., "Real-Time CARS Imaging Reveals a Calpain-Dependent Pathway for Paranodal Myelin Retraction during High-Frequency Stimulation", PLoS ONE, vol. 6, Issue 3 (Mar. 3, 2011): 17176, 11 pgs., doi:10.1371/journal.pone.0017176.
International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Preliminary Report for International Application No. PCT/AU2019/050278, dated Sep. 29, 2020, 7 pgs.
International Preliminary Report for International Application No. PCT/AU2019/050384, dated Oct. 27, 2020, 8 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2012/001441, Report dated May 27, 2014, 10 pgs.

(56) References Cited

OTHER PUBLICATIONS

International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, date dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 Pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16 Pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
International Search Report and Written Opinion for International Application No. PCT/AU2017/050296, Search completed Jul. 28, 2017, dated Jul. 28, 2017, 10 Pgs.
International Search Report and Written Opinion for International Application No. PCT/AU2017/050647, Search completed Sep. 29, 2017, dated Sep. 29, 2017, 13 Pgs.
International Search Report and Written Opinion for International Application No. PCT/AU2019/050384, Search completed Jun. 25, 2019, dated Jun. 25, 2019, 15 pgs.
International Search Report and Written Opinion for International Application No. PCT/AU2019/051385, Search completed Mar. 24, 2020, dated Mar. 24, 2020, 8 Pgs.
International Search Report and Written Opinion for International Application No. PCT/AU2015/050215, Search completed Jul. 30, 2015, dated Jul. 30, 2015, 8 Pgs.
International Search Report and Written Opinion for International Application No. PCT/AU2018/050278, Search completed Jun. 18, 2018, dated Jun. 18, 2018, 12 Pgs.
International Search Report for Australian Application 2011901829 Search Completed Feb. 6, 2012, dated Feb. 7, 2012, 3pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2019/051151, International Filing Date Oct. 22, 2019, Search Completed Feb. 24, 2020, dated Feb. 24, 2020, 9 pgs.
International Search Report for International Application No. PCT/AU2019/051160, International Filing Date Oct. 23, 2019, Search Completed Jan. 28, 2020, dated Jan. 28, 2020, 13 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
International Search Report for International Application No. PCT/AU2019/051163, International Filing Date Oct. 23, 2019, Search Completed Jan. 21, 2020, dated Jan. 31, 2020, 8 pgs.
International Search Report for International Application No. PCT/AU2019/051197, International Filing Date Oct. 30, 2019, Search Completed Jan. 21, 2020, dated Jan. 21, 2020, 15 pgs.

(56) References Cited

OTHER PUBLICATIONS

International Search Report for International Application No. PCT/AU2019/051210, International Filing Date Nov. 2, 2019, Search Completed Feb. 4, 2020, dated Feb. 4, 2020, 10 pgs.

International Type Search Report for International Application No. AU 2015902393, Search completed May 16, 2016, dated May 16, 2016, 8 Pgs.

Jang et al., "Single Channel Signal Separation Using Time-Domain Basis Functions", IEEE Signal Processing Letters, Jun. 2003, vol. 10, No. 6.

Jang et al., "A Maximum Likelihood Approach to Single-channel Source Separation", Journal of Machine Learning Research 4 (2003) 1365-1392.

Japanese Office Action for Application No. 2017-546830, dated Feb. 20, 2020, 5 pages with English translation.

Japanese Office Action for Application No. 2017-553090, dated Mar. 16, 2020, 12 pages with English translation.

Japanese Office Action for Application No. 2018-552138, dated Mar. 1, 2021, 7 pages with English translation.

Japanese Office Action for Application No. 2018-513699, dated Jun. 8, 2020, 7 pages with English translation.

Jeffrey et al., "A reliable method for intracranial electrode implantation and chronic electrical stimulation in the mouse brain", BMC Neuroscience. Biomed Central. London, GB. vol. 14, No. 1, Aug. 6, 2013 (Aug. 6, 2013), pp. 1-8.

Jones et al., "Scaling of Electrode-Electrolyte Interface Model Parameters in Phosphate Buffered Saline", IEEE Transactions on Biomedical Circuits and Systems, 2015, vol. 9, No. 3, pp. 441-448.

Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi:10.1109/IEMBS.20113.6091671.

Kent et al., AR, "Recording evoked potentials during deep brain stimulation: development and validation of instrumentation to suppress the stimulus artefact", J Neural Eng., Jun. 2012, vol. 9, No. 3, 036004, doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions On Biomedical Engineering, Aug. 2003, vol. 50, No. 8, pp. 999-1011.

Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi: 10.1016/S0306-4522(98)00022-0.

Kopelman et al., "Attempted Reversible Sympathetic Ganglion Block by an Implantable Neurostimulator", Interactive Cardiovascular and Thoracic Surgery, Feb. 7, 2012, vol. 14, Issue 5, pp. 605-609, doi:10.1093/icvts/ivr137.

Krames et al., "Neuromodulation", 1st Edition, Academic Press, 2009, pp. 540-541.

Krarup, Christian, "Compound sensory action potential in normal and pathological human nerves", Muscle & Nerve, Apr. 2004, vol. 29, No. 4, pp. 465-483,.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Sep. 11, 1999, vol. 53, No. 4, pp. 871-874, doi:10.1212/WNL.53.4.871.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Laird-Wah, "Improving Spinal Cord Stimulation: Model-Based Approaches to Evoked Response Telemetry", UNSW, Aug. 2015.

Lempka, Scott, "The Electrode-Tissue Interface During Recording and Stimulation in the Central Nervous System", Thesis, 155 pgs., published May 2010.

Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.

Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Macefield, "Spontaneous and Evoked Ectopic Discharges Recorded from Single Human Axons", Muscle & Nerve 21, No. 4, Apr. 1998, pp. 461-468.

Mah Nam et al., "Measurement of the current-distance relationship using a novel refractory interaction technique", J. Neural Eng, 6(2): 036005, published May 20, 2009, 22 pgs.

Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.

Markandey, Vishal, "ECG Implementation on the TMS320C5515 DSP Medical Development Kit (MOK)", Texas Instruments Application Report Jun. 2010, 35 pgs.

Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.

Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.

Medtronic, Spinal Cord Stimulation, RestoreSensor Neurostimulator, Features and Specification: Specification, Printed Jun. 16, 2014, 2 pgs.

Medtronic, Spinal Cord Stimulation, RestoreSensor Neurostimulator, Features and Specification: Summary Printed Jun. 16, 2014, 1 pg.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Niazy et al., "Removal of FMRI environment artifacts from EEG data using optimal basis sets", NeuroImage 28 (2005) 720-737.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.

North et al., "Prognostic value of psychological testing in patients undergoing spinal cord stimulation: a prospective study", Neurosurgery, Aug. 1, 1996, vol. 39, Issue 2, pp. 301-311, https://doi.org/10.1097/00006123-199608000-00013.

Oakley et al., "Spinal Cord Stimulation: Mechanisms of Action", Spine 27, No. 22, Nov. 15, 2002, pp. 2574-2583.

(56) References Cited

OTHER PUBLICATIONS

Oakley et al., "Transverse Tri polar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Office Action for Chinese Patent Application No. 201680020725.4, dated Mar. 16, 2020, 8 pgs.
Oh et al., "Long-term hardware-related complications of deep brain stimulation", Neurosurgery, vol. 50, No. 6, Jun. 2002, pp. 1268-1274, discussion pp. 1274-1276.
Olin et al., "Postural Changes in Spinal Cord Stimulation Perceptual Thresholds", Neuromodulation, vol. 1, No. 4, 1998, pp. 171-175.
Opsommer, E. et al., "Determination of Nerve Conduction Velocity of C-fibres in Humans from Thermal Thresholds to Contact Heat (Thermode) and from Evoked Brain Potentials to Radiant Heat ($CO_2$ Laser)", Neurophysiologie Clinique 1999, vol. 29, pp. 411-422.
Orstavik, Kristin et al., "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, 1109-1120, doi: 10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Parker et al., "Electrically Evoked Compound Action Potentials Recorded From the Sheep Spinal Cord", Neuromodulation, vol. 16, 2013, pp. 295-303.
Partial European Search Report for European Application No. 16775966.1, Search completed Oct. 26, 2018, dated Nov. 6, 2018, 11 Pgs.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Peterson et al., "Stimulation artifact rejection in closed-loop, distributed neural interfaces", ESSCIRC, 42nd European Solid-State Circuits Conference, Lausanne, 2016, pp. 233-235.
Rattay, "Analysis of Models for External Stimulation of Axons", IEEE Transactions On Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1 (S1), 2011, pp. 61-63.
Ridder et al., "Burst Spinal Cord Stimulation for Limb and Back Pain", World Neurosurgery, 2013, 9 pgs.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Roy, S. H. et al., "Effects of Electrode Location on Myoelectric Conduction Velocity and Median Frequency Estimates", J. Appl. Physiol. 61 (4), 1986, pp. 1510-1517.
Sa Yen Ko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Struijk et al., "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Struijk, "The Extracellular Potential of a Myelinated Nerve Fiber in an Unbounded Medium and in Nerve Cuff Models", Biophysical Journal vol. 71 Jun. 1997 2457-2469.
Sufka et al., "Gate Control Theory Reconsidered", Brain and Mind, 3, No. 2, 2002, pp. 277-290.
Takahashi et al., "Classification of neuronal activities from tetrode recordings using independent component analysis", Neurocomputing, (2002), vol. 49, Issues 1-4, 289-298.
Tamura et al., "Increased Nodal Persistent $Na+$ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., Dorsal Root Entry Zone (DREZ) Localization Using Direct Spinal Cord Stimulation Can Improve Results of the DREZ Thermocoagulation Procedure for Intractable Pain Relief, Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., Lan Kamp, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

(56) References Cited

OTHER PUBLICATIONS

Woessner, "Blocking Out the Pain, Electric Nerve Block Treatments for Sciatic Neuritis", Retrieved from: http://www.practicalpainmanagement.com/pain/spine/radiculopathy/blocking-outpain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Wu et al., "Changes in A13 Non-nociceptive Primary Sensory Neurons in a Rat Model of Osteoarthritis Pain", Molecular Pain 6, No. 1 (Jul. 1, 2010): 37, doi: 10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L. , "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al. , "Recording monophasic action potentials using a platinumelectrode ablation catheter", Europace. Oct. 2000; 2(4):312-319.
Zhang et al., "Automatic Artifact Removal from Electroencephalogram Data Based on A Priori Artifact Information", BioMed research international. 2015. 720450. Aug. 25, 2015 DOI: https://doi.org/10.1155/2015/720450.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

METHOD AND APPARATUS FOR APPLICATION OF A NEURAL STIMULUS

CROSS-REFERENCE TO RELATED APPLICATIONS

This application is a continuation of U.S. patent application Ser. No. 17/576,060, filed on Jan. 14, 2022, which is a continuation of U.S. patent application Ser. No. 17/514,650, filed on Oct. 29, 2021, which is a continuation of U.S. patent application Ser. No. 17/501,823, filed on Oct. 14, 2021, which is a continuation of U.S. patent application Ser. No. 17/489,710, filed on Sep. 29, 2021, which is a continuation of U.S. patent application Ser. No. 17/478,793, filed on Sep. 17, 2021, which is a continuation of U.S. patent application Ser. No. 17/031,749, filed on Sep. 24, 2020, which is a continuation of U.S. patent application Ser. No. 15/846,069, filed on Dec. 18, 2017, which is a continuation of U.S. patent application Ser. No. 14/844,929, filed on Sep. 3, 2015 and issued as U.S. Pat. No. 9,872,990, which is a continuation of U.S. patent application Ser. No. 14/117,586, filed on May 13, 2014 and issued as U.S. Pat. No. 9,155,892 on Oct. 13, 2015, which is a U.S. National Stage Application under 35 U.S.C. § 371 of International Application No. PCT/AU2012/000515, filed on May 11, 2012, which claims priority to Australian Provisional Patent Application No. AU2011901828 filed May 13, 2011 and Australian Provisional Patent Application No. AU2011901829 filed May 13, 2011, all of which are incorporated herein by reference.

TECHNICAL FIELD

The present invention relates to application of a neural stimulus, and in particular relates to applying a neural stimulus in a controlled manner by using one or more electrodes implanted proximal to the neural pathway. The present invention also relates to controlling a neural response to a stimulus, and in particular relates to measurement of a compound action potential by using one or more electrodes implanted proximal to the neural pathway, in order to provide feedback to control subsequently applied stimuli.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Aδ fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of applying a neural stimulus with an implanted electrode array, the method comprising:
  using the electrode array to applying a sequence of stimuli configured to yield a therapeutic effect while suppressing psychophysical side effects, the stimuli sequence configured such that a first stimulus recruits a portion of the fibre population, and a second stimulus is delivered within the refractory period following the first stimulus and the second stimulus being configured to recruit a further portion of the fibre population.

According to a second aspect the present invention provides a device for applying a neural stimulus, the device comprising:
  at least one electrode configured to be positioned alongside a neural pathway; and
  a control unit configured to apply a sequence of neural stimuli which are configured to yield a therapeutic effect while suppressing psychophysical side effects, the stimuli sequence configured such that a first stimulus recruits a portion of the fibre population, and a second stimulus is delivered within the refractory period following the first stimulus and the second stimulus being configured to recruit a further portion of the fibre population.

By providing for a second stimulus to be delivered in the neural refractory period following the first stimulus, the present invention provides for de-correlated, or less correlated, fibre responses to be evoked by such stimuli.

The sequence of neural stimuli may comprise more than two stimuli, each being delivered in the refractory period following a previous stimulus in the sequence.

The sequence of neural stimuli may comprise stimuli of ascending amplitude.

The sequence of neural stimuli may be applied sequentially by a single electrode.

Alternatively, the sequence of neural stimuli may be applied sequentially by more than one electrode. In such embodiments, the second stimulus is preferably delivered at a time after the first stimulus which allows for cessation of the first stimulus and allows for propagation of a first neural response evoked by the first stimulus from the first electrode to the second electrode, so that the second stimulus is delivered during a refractory period of neurons proximal to the second electrode after activation of those neurons by the evoked neural response from the first stimulus.

Additionally or alternatively, in some embodiments the sequence of neural stimuli may be applied by consecutive electrodes positioned along an electrode array.

In embodiments where the sequence of neural stimuli is applied sequentially by more than one electrode, the timing of the respective stimuli in the sequence may be controlled in order to cause spatiotemporal alignment of the respective evoked responses propagating in a first direction along the nerve fibre to thereby cause correlation and summation of evoked responses in the first direction, while causing spatiotemporal misalignment of the respective evoked responses propagating in a second direction opposite the first direction along the nerve fibre, to thereby decorrelate evoked responses propagating in the second direction. Such embodiments may be advantageous in decorrelating evoked potentials propagating toward the brain, where it is desired to avoid or minimise any percept from the stimuli.

In some embodiments of the invention, the sequence of neural stimuli may be followed by a single stimulus which is not applied during the refractory period of any preceding stimulus, and which is not closely followed by any subsequent stimulus in the refractory period of the single stimulus. Such embodiments may be applied in order to enable an evoked response measurement to be made following the single stimulus, to enable ongoing refinement of stimulus parameters of the sequence of neural stimuli.

According to a third aspect the present invention provides a computer program product comprising computer program code means to make a computer execute a procedure for applying a neural stimulus with an implanted electrode array, the computer program product comprising computer program code means for carrying out the method of the first aspect.

According to a fourth aspect the present invention provides an automated method of controlling a neural stimulus, the method comprising:
  applying the neural stimulus as defined by a set of parameter values;
  measuring a neural response evoked by the stimulus;
  comparing one or more characteristics of the measured neural response to a desired response;
  altering one or more of the parameter values; and
  iteratively performing the applying, measuring, comparing and altering, in order to explore a parameter search space having at least two variable parameters, to identify a set of parameter values which evokes a neural response best matching the desired response.

According to a fifth aspect the present invention provides an implantable device for applying a neural stimulus, the device comprising:
  a plurality of electrodes including one or more nominal stimulus electrodes and one or more nominal sense electrodes;
  a stimulus source for providing a stimulus to be delivered from the one or more stimulus electrodes to neural tissue;
  measurement circuitry for recording a neural signal sensed at the one or more sense electrodes; and
  a control unit configured to control application of a neural stimulus as defined by a set of parameter values, the control unit configured to measure a neural response evoked by the stimulus, the control unit configured to compare one or more characteristics of the measured neural response to a desired response, the control unit configured to alter one or more of the parameter values, and the control unit configured to iteratively perform the applying, measuring, comparing and altering, in order to explore a parameter search space having at least two variable parameters, to identify a set of parameter values which evokes a neural response best matching the desired response.

The set of parameter values defining the stimulus may comprise one or more of: stimulus current, pulse amplitude, phase duration, interphase gap duration, pulse shape, repetition rate, electrode selection and electrode combination.

In preferred embodiments, the stimulus parameters are refined on an ongoing basis in order to adaptively control the stimuli in response to postural changes of the user. In such embodiments, the parameter search space may be reassessed on a regular basis, for example once a second. Alternatively the parameter search space may be reassessed only in response to a trigger, such as a signal from an accelerometer which has detected patient movement, thereby avoiding excessive power consumption at times when the patient is not moving.

In some embodiments of the invention, the one or more characteristics of the measured neural response may comprise a measure of neural fibre conduction velocity. In such embodiments, the measured neural fibre conduction velocity may be used to determine selectivity of recruitment of a target fibre class, for comparison to a desired fibre class recruitment ratio or range as defined by the desired response. For example for pain suppression the desired response may be defined as requiring high selectivity of Aβ fibres.

Additionally or alternatively, the one or more characteristics of the measured neural response may comprise a measure of neural response amplitude. In such embodiments, the parameter search space may be explored by iteratively applying stimuli and measuring neural responses in order to identify a "perception" threshold for stimulus current, below which no evoked response arises from stimulus. Additionally or alternatively, such embodiments may explore the parameter search space in order to identify a "maximum" or "comfort" threshold at a current level above which a slow response first starts to arise, by assessing the neural response amplitude at an expected time of occurrence of any slow response, such as about 3-4 ms after stimulation.

In embodiments where the one or more characteristics of the measured neural response comprise a measure of neural response amplitude, the stimulus parameters may be refined on an ongoing basis in order to adaptively control the stimuli in response to postural changes of the user so as to maintain the evoked response amplitude at a fixed point above the perception threshold. Such embodiments may thus enable a controlled level of neural recruitment even during user postural changes, and may also be of benefit in avoiding misalignment of induced paraesthesia from a preferred location. To maximally align induced paraesthesia with a preferred location, the stimulus parameters may include a body map setting out the location of effects of stimuli when applied by each electrode of an electrode array. The body map may be predefined and based on patient feedback to clinical trial stimuli, or may be subject to revision during ongoing use for example by way of user input upon a remote control of the implant.

In embodiments where the one or more characteristics of the measured neural response comprise a measure of neural response amplitude, the stimulus parameters may be refined on an ongoing basis in order to maintain stimuli at a sub-threshold level, for example as may be intended for non-paraesthesia therapeutic use.

In some embodiments, the one or more characteristics of the measured neural response may comprise measures of variations of an amplitude of a fast neural response in response to varied stimulus current. In such embodiments, a comfort level threshold may be defined relative to an inflection point marking decelerating growth of the fast response amplitude in response to increasing stimulus current. Such embodiments recognise that deceleration in the growth of the fast response amplitude in response to increasing stimulus current generally reflects where further recruitment starts to fall and undesirable side effects begin such as onset or increase of a slow neural response.

In some embodiments, where the one or more characteristics of the measured neural response comprise measures of variations of an amplitude of a fast neural response in response to varied stimulus current, the stimulus may be maintained within a linear range of the neural recruitment vs. current curve, and an electrode-to-fibre distance d may be estimated. An estimate for d may be obtained by measuring the amplitude ($R_{e1p1}$, $R_{e5p1}$) of the neural response as measured at two spaced apart sense electrodes (denoted e1 and e5) for a first stimulus, and measuring the amplitude ($R_{e1p2}$, $R_{e5p2}$) of the neural response at the two sense electrodes for the same stimulus after a change in d. This embodiment recognises that despite a scaling factor $S_s$ due to changed measurement sensitivity with d, these measurements permit the change in recruitment scaling factor $A_s$ in response to d to be calculated as:

$$(R_{e1p2}/R_{e1p1})-(R_{e5p2}/R_{e5p1})=A_s$$

Additionally or alternatively, the electrode to fibre distance d may in some embodiments be estimated by obtaining neural response amplitude measurements in response to at least two stimuli of differing current level, the stimuli being substantially within a linear range of the neural recruitment vs. current curve. Taking a linear extrapolation of the amplitude measurements to the x-axis (i.e. the point of zero neural response) provides an estimate of the stimulus current threshold.

In embodiments obtaining an estimate of the electrode to fibre distance d, this estimate may be used to influence stimulus current and/or to appropriately scale measured neural responses to compensate for altered measurement sensitivity, in order to maintain constant or controlled neural recruitment.

In some embodiments of the invention, the one or more characteristics of the measured neural response may comprise a measure of dispersion of the response relative to distance from the stimulus site. In such embodiments, changes in dispersion may be used as indication of changes in electrode-to-fibre distance d, wherein increased dispersion correlates to increased electrode-to-fibre distance d.

In some embodiments of the invention, the one or more characteristics of the measured neural response may comprise a measure of fast neural response peak position relative to stimulus. In some embodiments of the invention, the one or more characteristics of the measured neural response may comprise a measure of the fast neural response peak width. In such embodiments, the electrode-to-fibre distance d, and/or the neural recruitment efficacy, may be estimated by reference to peak position and/or peak width of the fast neural response, with a faster narrower peak reflecting greater recruitment and potentially a movement of the electrode towards the fibre.

In some embodiments of the invention, the one or more characteristics of the measured neural response may comprise a measure of spectral characteristics of the evoked response. In such embodiments, the electrode-to-fibre distance d may be determined by reference to the spectral characteristics, recognising that a transfer function of an action potential along a nerve fibre, and laterally to a sense electrode, depends on d. For example, changes in d may be detected and estimated by selecting two different frequencies which are prominent in the spectrum of the CAP, and examining the ratio between the two frequencies over time.

According to a sixth aspect the present invention provides a computer program product comprising computer program code means to make a computer execute a procedure for automated control of a neural stimulus, the computer program product comprising computer program code means for carrying out the method of the fourth aspect.

BRIEF DESCRIPTION OF THE DRAWINGS

An example of the invention will now be described with reference to the accompanying drawings, in which:

FIG. 2a shows the Aβ response amplitude growth functions for stimulation of the sheep spinal cord at 40, 80 and 120 μs, while

DESCRIPTION OF THE PREFERRED EMBODIMENTS

Figure 1:
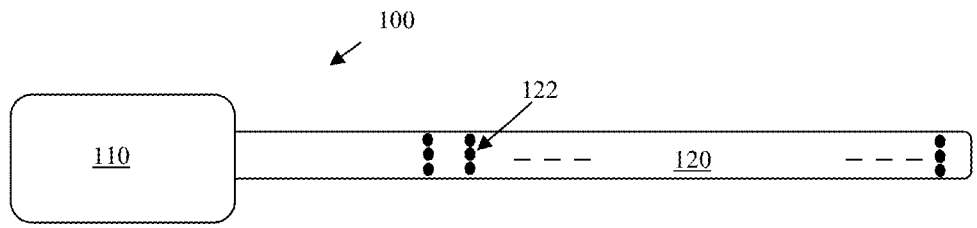
FIG. 1 illustrates an implantable device suitable for implementing the present invention.

FIG. 1 illustrates an implantable device 100 suitable for implementing the present invention. Device 100 comprises an implanted control unit 110, which controls application of a sequence of neural stimuli in accordance with the present invention. In this embodiment the unit 110 is also configured to control a measurement process for obtaining a measurement of a neural response evoked by a single stimulus delivered by one or more of the electrodes 122. Device 100 further comprises an electrode array 120 consisting of a three by eight array of electrodes 122, each of which may be selectively used as either the stimulus electrode or sense electrode, or both.

The activation and simultaneous suppression of different areas of tissue is highly desired for treatment of a number of neurological disorders. The activation of micturition or defection without contraction of the sphincter is highly desirable for treatment of incontinence. The goal of stimulation of the spinal cord is to block transmission of pain signals from Aδ and C fibres, via the inhibitory effect of the activation of Aβ fibres. The ascending Aβ fibres produce a psycho-physiological response which results in the paraesthesia (described as tingling by recipients). A number of ways to reduce or eliminate this effect have been suggested. It has been reported that burst mode stimulation or continuous stimulation at high frequencies can produce pain relief without accompanying paraesthesia, however the mechanisms are not clear.

One possible explanation is that the high frequency stimulation results in a highly uncorrelated neural firing pattern in the ascending Aβ tracts. High frequency stimulation results in the continuous activation of the fibres and produces a randomised firing pattern. The recovery time (refractory period) between each fibre is slightly different and if a depolarisation potential is present as the fibre comes out of refractory period, it will depolarise again, but not synchronised with other fibres which may still be in their refractory periods. The net result is a randomisation of the firing pattern and a return of the stochastic response in the fibre.

Figure 2A:
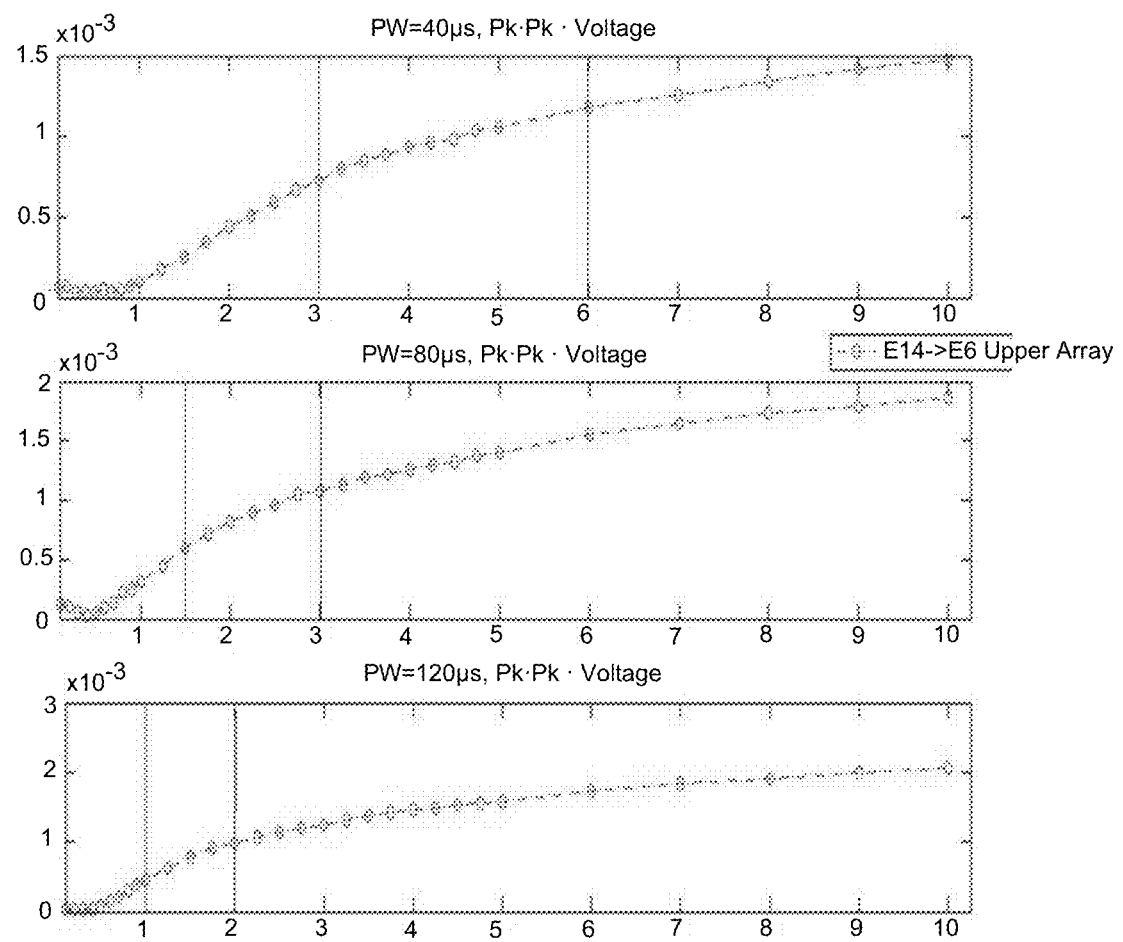
Figure 2B:
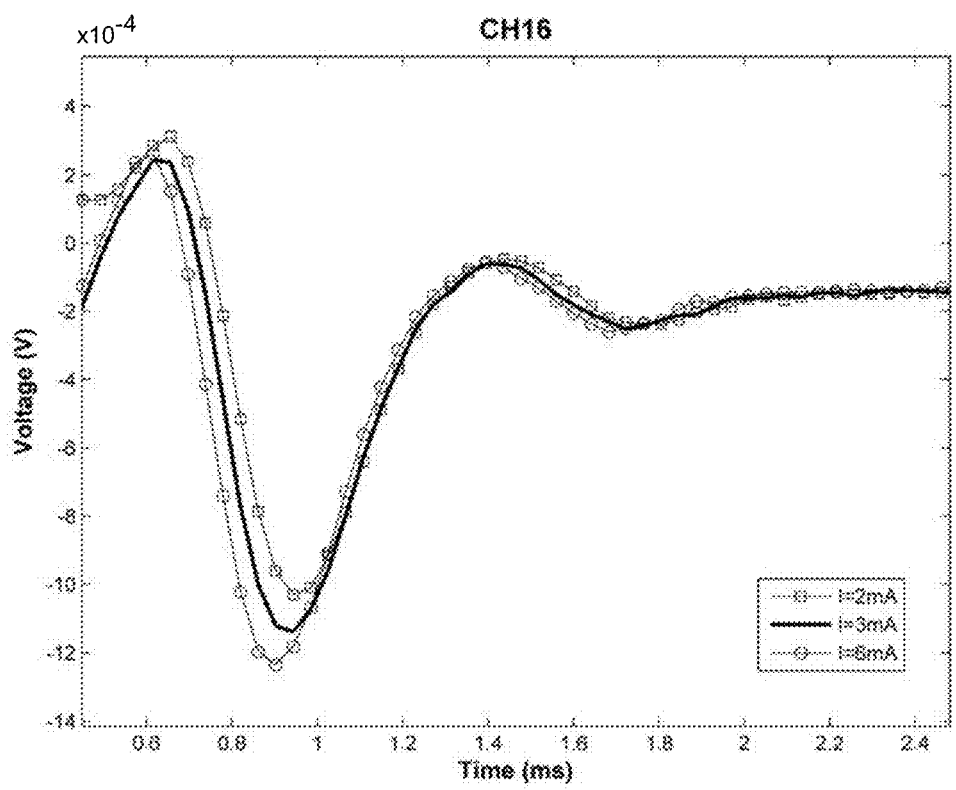
FIG. 2b shows the compound action potential recorded at equivalent charges for the three different pulse widths.

Measurements of the evoked neural response provide a direct measure of the degree of correlation of the firing pattern. FIG. 2a shows the Aβ response amplitude growth functions with respect to stimulus amplitude, for stimulation of the sheep spinal cord at 40, 80 and 120 μs. The recruitment is related to charge and so stimulation at 1 mA for 120 μs produces an equivalent charge for stimulation at 3 mA for 40 μs, with vertical lines highlighting two respective points of equal charge delivery for each trace. FIG. 2b shows the compound action potential recorded at equivalent charges for the three different pulse widths. The peak height is smaller and the evoked response peak is wider at the equivalent charge for the longer pulse width than for the shorter pulse width, and this is indicative of a less correlated evoked response.

The probability of any single fibre responding is a function of the properties and history of the fibre and the amplitude of the current pulse. Although short and long pulses for an equivalent charge may recruit the same number of fibres the longer lower current amplitude pulse will recruit the fibres over a longer time scale than the higher current shorter pulse width.

Patients report a preference for stimulation with longer pulse widths and the reason for this preference may be because the perceptual side effect is lower, because there is a lower correlation between the fibres firing. Given this observation, highly uncorrelated responses may give rise to much lower psycho-physical side effects such as tingling sensations and paraesthesia. The evoked responses measured for the longer pulse widths are broader in FIG. 2b, indicating less correlation in the firing pattern.

Measurement of the evoked response provides a unique way to assess the degree of correlation amongst fibres in a group, as the peak width and amplitude of the measured response directly relates to the degree of timing synchronisation of the single fibre action potentials which sum to form the compound action potential. The goal of stimulus design is to achieve a high level of recruitment at the segmental level and a low level of correlation for the ascending segments. The neural response measurement obtained at each sense electrode may be conducted in accordance with the techniques set out in Daly (2007/0225767), the content of which is incorporated herein by reference. Additionally or alternatively, the neural response measurement may be conducted in accordance with the techniques set out in Nygard (U.S. Pat. No. 5,785,651), the content of which is incorporated herein by reference. Additionally or alternatively, the neural response measurement may be conducted in accordance with the techniques set out in the Australian provisional patent application filed simultaneously herewith in the name of National ICT Australia Ltd entitled "Method and apparatus for measurement of neural response".

The degree of correlation within an evoked response can be measured with such techniques, and pulse sequences can be designed to produce evoked responses of a desired character. A typical recruitment curve is shown in FIG. 2a. The strength of the Aβ potentials directly relates to the number of fibres recruited, and therefore stimulation at successive larger and larger pulse amplitudes will recruit successively more fibres. If the pulses are timed so that they occur within the refractory period of the excited neurons from the previous pulse then different sub populations of neurons can be selected with each pulse.

The timing of each pulse can be so arranged so that the travelling CAPs from each individual pulse cancel each other as they sum at some distance from the stimulation site. This indicates the degree of desynchronisation between the fibres, and as the sensory input is based on correlation of firing patterns the sensation (paraesthesia) is reduced. However, the activation of the inhibitory effect of the Aβ fibres at the segmental level is not reduced, permitting Aβ inhibition of Aδ and C propagation to occur, as desired.

Figure 3:
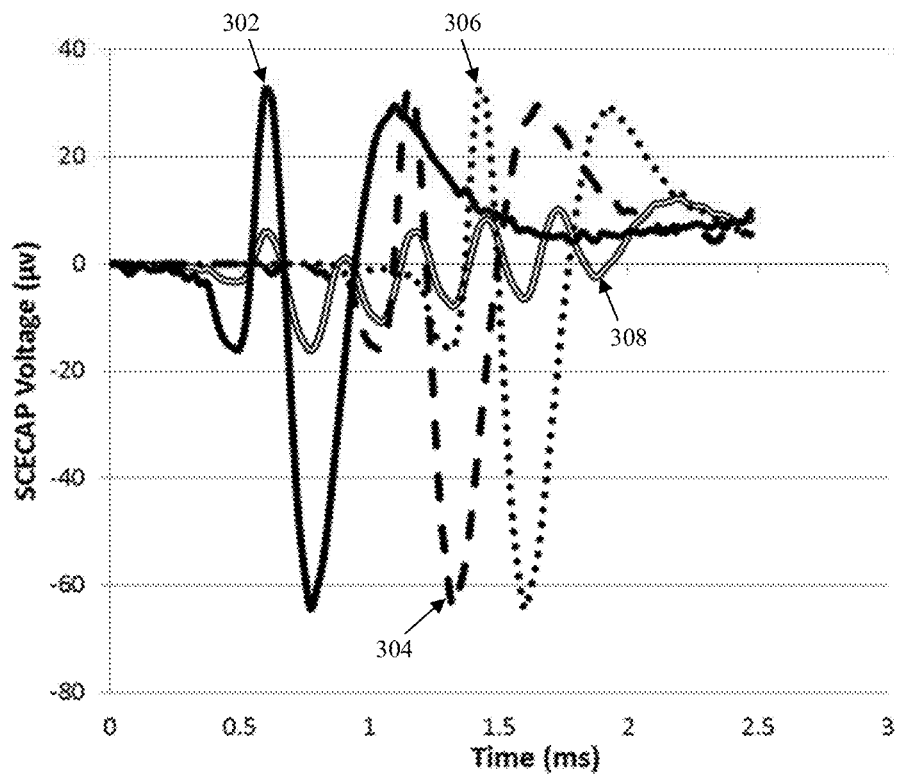
FIG. 3 illustrates summation of a sequence of overlapped neural responses.

FIG. 3 illustrates the principle of applying a sequence of neural stimuli and allowing the respective evoked responses 302, 304, 306 to propagate along the fibre. The numerical summation of five such partially overlapping compound action potentials, of which only three appear in FIG. 3, is shown at 308. FIG. 3 shows the effect of the summation of the evoked response from five pulses with the timing intervals between the pulses so arranged as result in the arrival of the evoked response waveform at a designated point along the electrode array such that the averaged signal recorded at that point is minimised. For the data shown in FIG. 3 the timing difference between each cathodic pulse is 0.3 ms.

Figure 4:
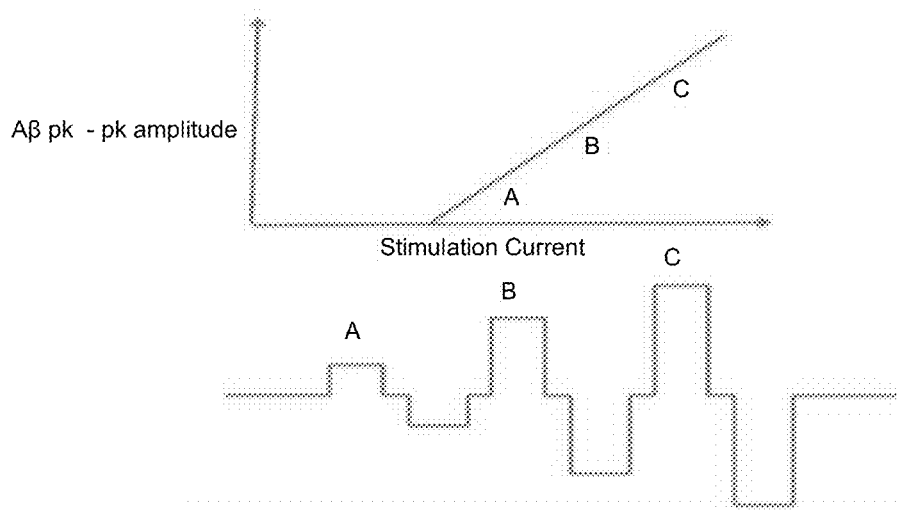
FIG. 4 is a schematic illustration of a potential pulse sequence and the amplitude growth curve associated with the sequence.

FIG. 4 is a schematic illustration of a potential pulse sequence (lower) and the amplitude growth curve associated with the sequence (upper). Current levels A-C are represented on both portions of FIG. 4. The initial pulse of amplitude A can be expected to recruit only a portion of the available population. Application of the subsequent stimulus of greater amplitude can then be expected to recruit a further portion, but not all, of the available neural population, even though stimulus B is applied during the refractory period after stimulus A. Similarly, stimulus C can be expected to recruit a further portion of the available neural population. C may be applied during the refractory period of stimulus B only, or possibly within the refractory period of both stimuli A and B. The sequence of neural stimuli A-B-C can thus be expected to recruit perhaps a similar amount of the available neural population as would stimulus C if applied alone, however the progressive recruitment of portions of the neural population at progressive times provides for a significantly decorrelated evoked response as compared to the response resulting from a single stimulus of amplitude C.

The concept of a selection of stimulus sequences based on the ERT recorded parameters can be greatly extended. For instance the example of FIG. 4 demonstrates achieving an uncorrelated ensemble response in the fibre population being stimulated.

Figure 5:
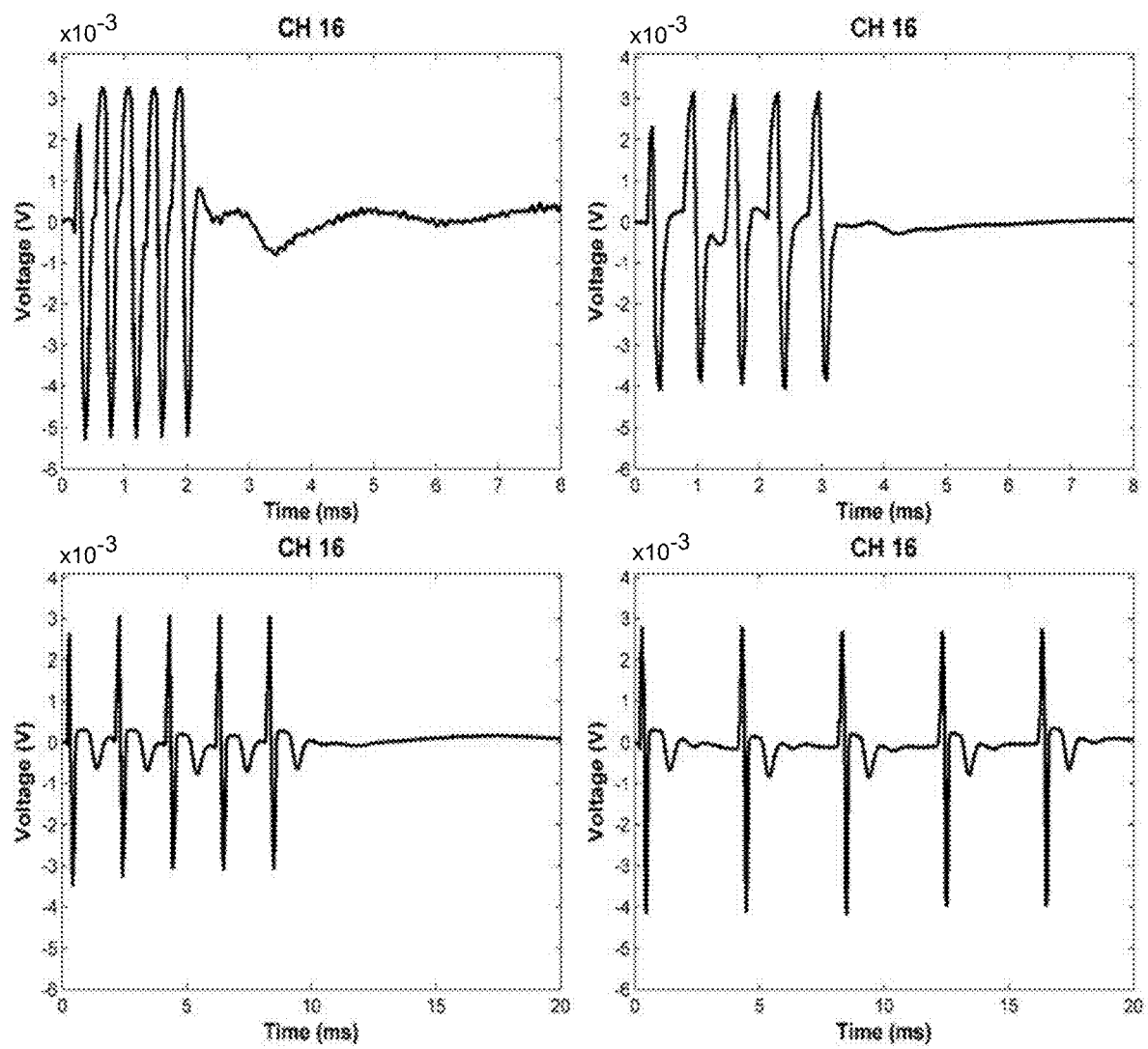
FIG. 5 illustrates ERT responses to bursts of stimulation with differing frequencies.

FIG. 5 illustrates ERT responses to bursts of stimulation with differing frequencies. The degree of correlation can be inferred from the ERT signal. A normal stimulus can be used to assess the stimulation response amplitude in the absence of any further desynchronising pulses. The amplitude of the single probe pulse is adjusted to represent the total charge delivered over time for the corresponding desynchronising pulse train. The amplitude of the response measured from the single probe pulse represents a fully synchronised response. The desynchronising pulse train is then output and the response measured. The ratio of the two responses is proportional to the level of synchronisation and so can be used as a control parameter for adjusting the characteristics of the device. For instance the control parameter may be adjustable by the patient to allow the patient to adjust the level of perceived paraesthesia. The control variable may also be used by the system for detection of a change of state in the neural tissue for a diagnostic purpose.

A single non-decorrelating stimulus can be applied to the nerve by the device periodically or occasionally in order to elicit an evoked response which is then used as the input to the control loop. This probe stimulus can be adjusted so that its charge is equivalent to the charge presented by the desynchronising stimuli. The frequency of the probe pulse to desynchronising pulses can then be adjusted to minimise the perceptual side effects. The probe frequency can also be adjusted on demand, responding more rapidly to changes in movement, for example.

Figure 6:
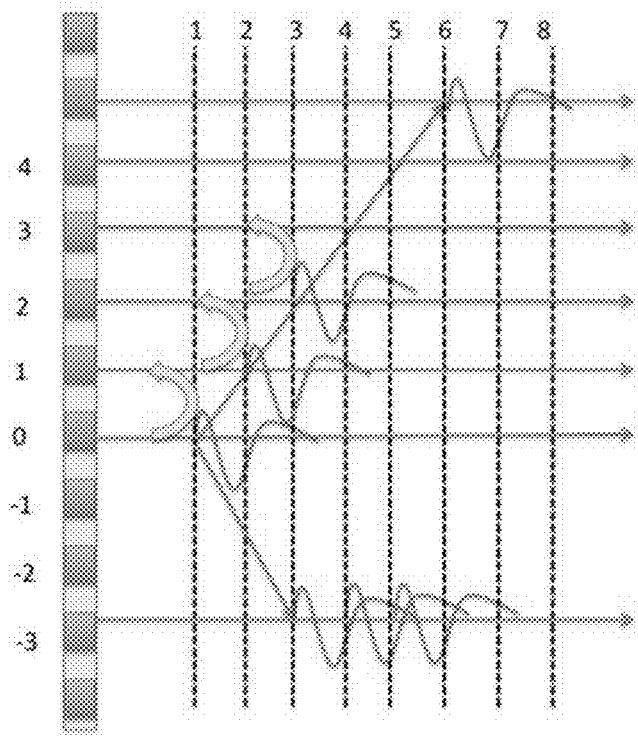
FIG. 6 illustrates a stimuli scheme to generate stimuli which result in synchronising Aβ activation in the antidromic direction and a desynchronising activity in the orthodromic direction.

Conduction of the compound action potentials occurs both orthodromically (up the spine) and antidromically (down the spine). Careful choice of stimulus design can be used to create a situation where the degree of synchronisation can be different in both directions, and controllably so. For example it may be desirable to generate stimuli which result in synchronising Aβ activation in the antidromic direction and a desynchronising activity in the orthodromic direction. One possible scheme for doing this is illustrated in FIG. 6. A stimulus pulse, preferably biphasic, is discharged at an electrode (electrode '0' indicated on the left side of FIG. 6). At some time interval later a $2^{nd}$ stimulus pulse is discharged between another two electrodes. For convenience this is illustrated in FIG. 6 as the electrode (number "1") adjacent to the first electrode. The $2^{nd}$ discharge is arranged so that it occurs in time and place such that its resultant CAP propagation to an electrode (e.g. '+6') in one direction (the upward direction in FIG. 6) sums with each other evoked CAP. In contrast, in the other direction (the downward direction in FIG. 6), the respective CAPs are misaligned and decorrelated for example when observed at electrode '−3'.

A possible means but not the only means to achieve such directional selectivity of CAP correlation is to arrange a series of stimulus pulses with an interpulse interval equal to the difference in propagation time required for desynchronisation of the CAP in the ascending direction.

Note that the order in which the stimuli are presented does not need to be sequential. The amplitudes of the individual stimuli can also be varied according to the scheme of FIG. 4. The timing of presentation can also be dithered to adjust the timing.

Figure 7:
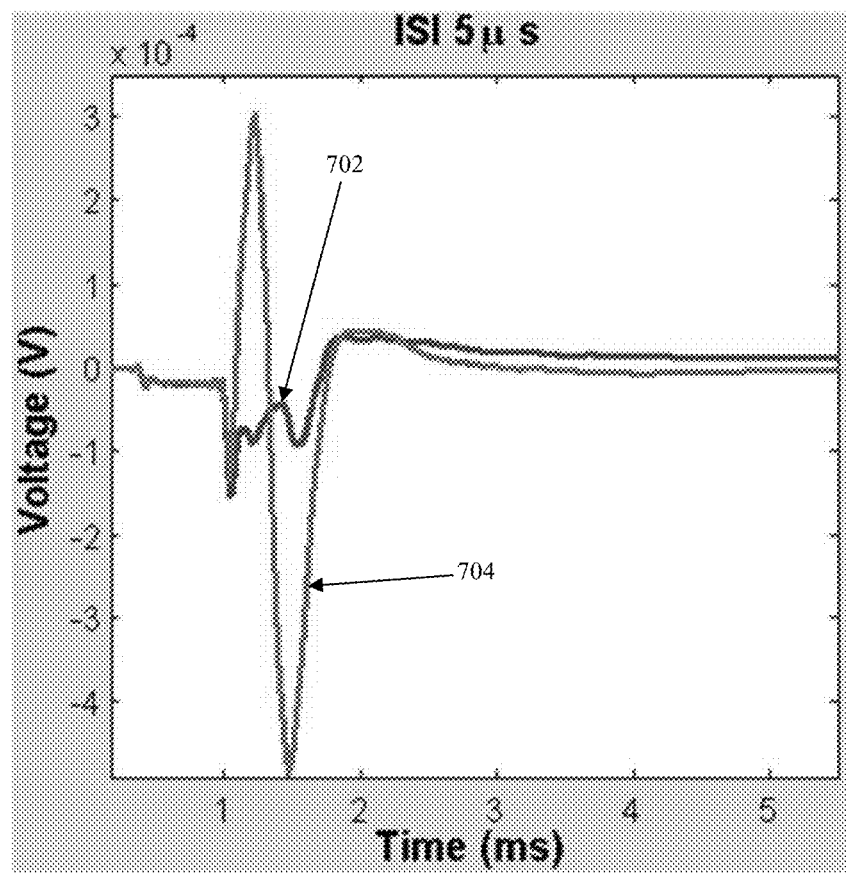
FIG. 7 illustrates experimental results obtained by applying a series of four stimuli of ascending amplitude on four adjacent electrodes to a sheep spinal cord.

FIG. 7 illustrates experimental results obtained by applying a series of four stimuli of ascending amplitude on four adjacent electrodes to a sheep spinal cord. Each stimulus was a tripolar stimulus for which the respective centre electrode was, in order, electrode E7, E8, E9 and E10, being the four centrally positioned electrodes of a 16 electrode linear electrode array. Each stimulus was biphasic with each phase having a pulse width of 20 μs, and the interphase gap being 10 μs. The stimuli were of ascending amplitude, being 2 mA, 2.5 mA, 3 mA and 3.5 mA respectively. The inter-stimulus interval between each successive pair of stimuli on the respective electrodes was 33 μs, so that the pulse-to-pulse time was 83 μs, to optimally correlate the net evoked response in the antidromic (ie caudal) direction. As can be seen in FIG. 7 the antidromic response 704 measured on electrode E16 was well correlated from the four constituent parts, and is of large amplitude. In contrast, the four orthodromic responses were effectively decorrelated and produced a net response 702 measured at electrode E3 which was of much reduced amplitude compared to response 704 travelling in the opposite direction, even though both were produced by the same burst of four stimuli.

Figure 8:
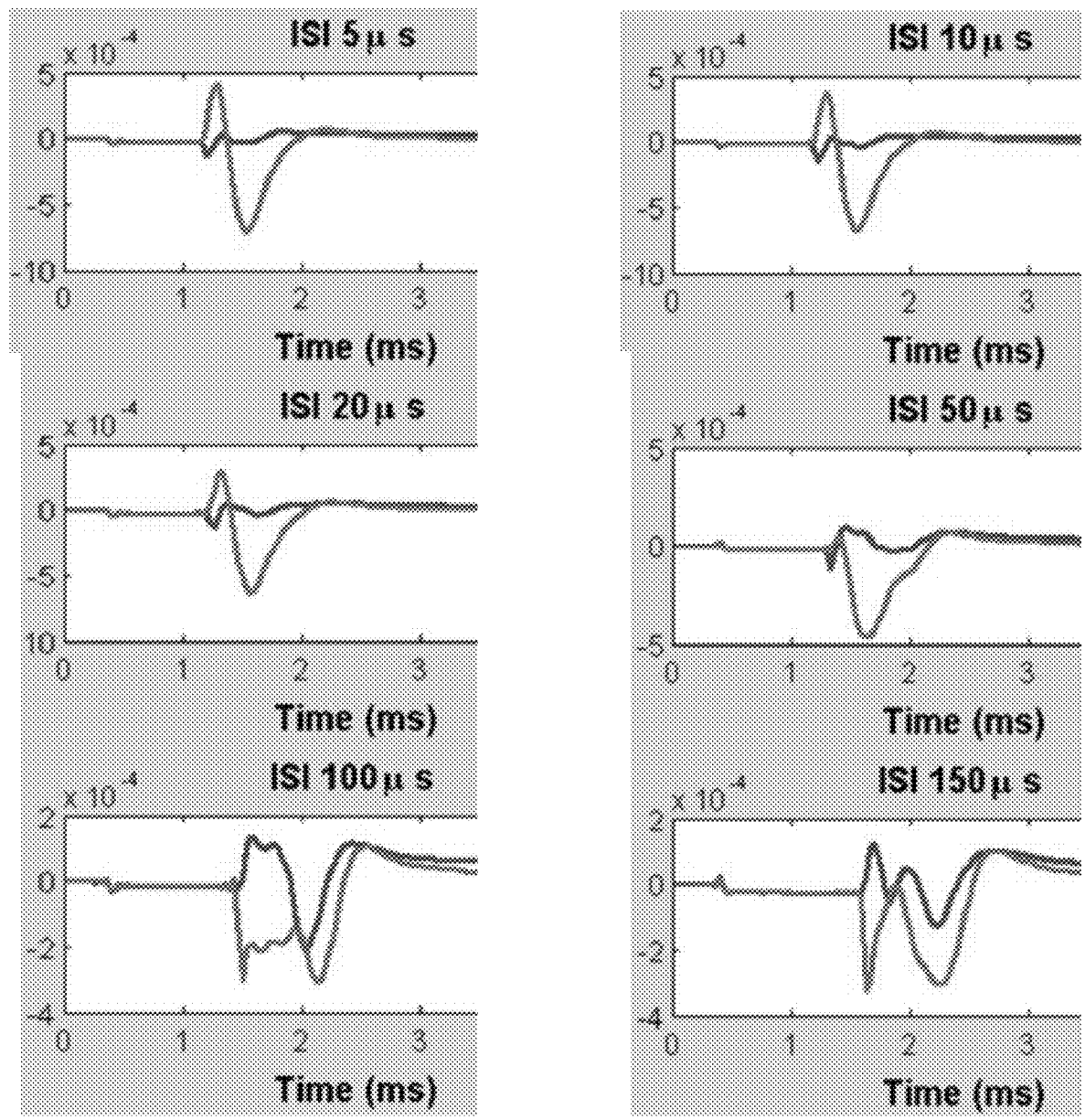
FIG. 8 illustrates experimental results obtained in response to stimuli bursts of different inter-stimulus intervals.
Figure 9:
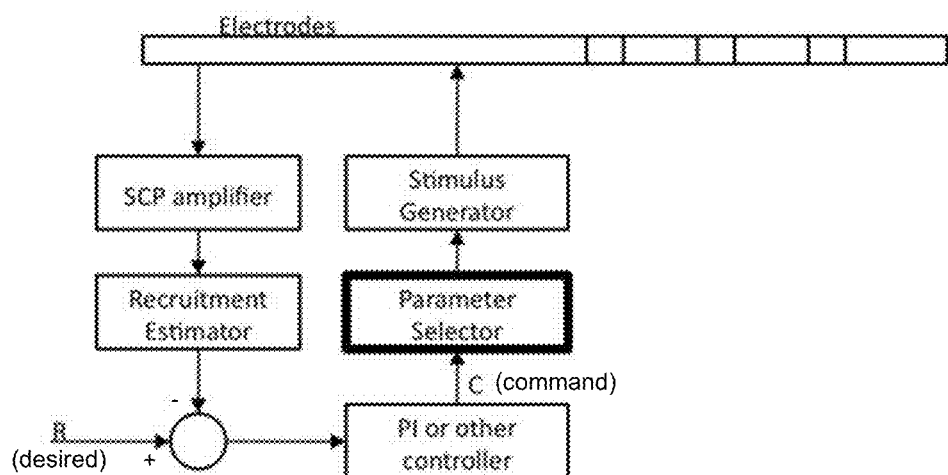
FIG. 9 illustrates a suitable feedback controller for controlling the parameters of the stimuli burst in an automated manner.

FIG. 8 shows the responses measured at different inter-stimulus intervals. As can be seen the inter-stimulus interval strongly affects efficacy of this technique, and so preferred embodiments provide a feedback loop in order to optimize this parameter, and all other stimulus parameters, in setting up the stimuli burst. FIG. 9 illustrates a suitable feedback controller for controlling the parameters of the stimuli burst in an automated manner, so as to use the measured evoked responses in each direction to determine the stimulus parameters required to achieve a desired directional effect. Such automated feedback permits the relatively large parameter space to be efficiently explored to identify optimal stimuli burst parameters.

Figure 10:
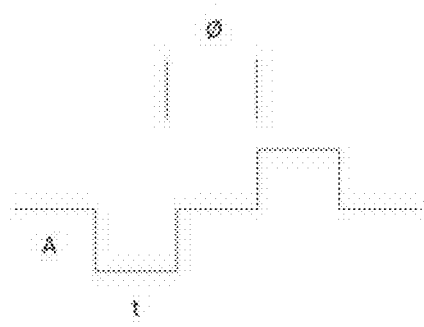
FIG. 10 is a schematic of a typical biphasic charged-balanced stimulus pulse.

Improvements in efficiency and recruitment selectivity are highly desirable. There have been two major types of stimulus waveforms used to generate propagating action potentials: voltage control and current control. Current control pulses are normally biphasic—current is passed from one electrode to another in the system, and then reversed. A typical biphasic charge-balanced stimulus pulse has an amplitude (A) and width (t) with an interphase gap Ø, as shown in FIG. 10. Such a pulse applied to the spinal cord produces an evoked response. The strength of the evoked response is related to the neural recruitment, and the shape of the evoked response is related to the distribution of fibre types being recruited. Considering the parameters A, t, Ø, it is possible to adjust these parameters in a systematic manner so as to obtain a desired evoked response output.

Figure 11:
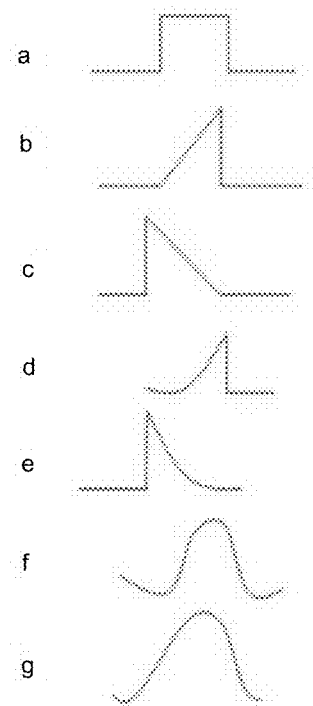
FIG. 11 illustrates a selection of pulse shapes which may be tested to determine the most efficient at producing depolarisation.

Moreover, the present invention recognises that non-rectangular pulses have an effect on the strength-duration relationships of recruitment. FIG. 11 illustrates a selection of the many different possible stimulus pulse shapes which may be tested to determine which is most efficient at producing depolarisation. The strength-duration curve relates the time for which a stimulus is applied to the nerve, to the recruitment level of the fibres in the nerve. The temporal recruitment responses for different fibres of different sizes depend on the pulse shape. A large number of large diameter fibres are recruited at the beginning of a square pulse (FIG. 11a), and an approximately constant uniform number of small fibres are then recruited over time as the pulse continues. In contrast, negative sloping waveforms (FIGS. 11c, 11e) recruit high numbers of both large and small diameter fibres. The adjustment of stimulation parameters for a spinal cord stimulator requires recruitment of Aβ fibres. Recruiting smaller fibres such as Aδ fibres may cause undesirable side effects.

If there is a wide range of different fibre diameters being recruited then the $(N_1^t\text{-}P_2^t)$ will spread out as the action potential propagates up the spinal cord. This is because as disparate fibre classes are recruited, the P-N-P morphology of the CAP is replaced by a more complicated waveform, which can generally be thought of as equivalent to the summation of one P-N-P wave per fibre class.

There are thus two salient parameters which may be focussed upon. First, the strength (amplitude) of the evoked response, which relates to the recruitment. Second, the evoked response dispersion which relates to the selectivity of fibre classes.

The present invention recognises that there are a number of ways to adjust the stimulus parameters (such as stimulus shape and amplitude) in order to optimise the selectivity and efficiency of recruitment. However, the past approach of optimising a stimulus on the basis of patient feedback is entirely impractical when the parameter search space is made so large as to include pulse shape, amplitude, interphase gap, and so on. Accordingly, to search for an optimally efficient set of stimulus pulse parameters, the present embodiment provides for automated optimisation of the stimulus pulse parameters based on measurement of the evoked response arising from test stimuli having varied stimulus parameters. The stimulus optimisation process in this embodiment occurs automatically, and may be completed within minutes and therefore performed regularly, as opposed to clinical optimisation.

There are a number of ways to adjust the stimulus parameters. In the present embodiment, the stimulus parameter search space is explored by iteratively applying stimuli and obtaining measurements of neural responses thereto, assessing how well the measured response confirms to a desired response, and refining the stimulus parameters in accordance with a genetic, heuristic or other search algorithm. A genetic algorithm, for example, may separate the parameter set into two sets of traits, and iteratively modify the contents of each set, whereby each iteration combines the traits of the more successful parameter values to form a new set of parameters for stimulus application.

Figure 12:
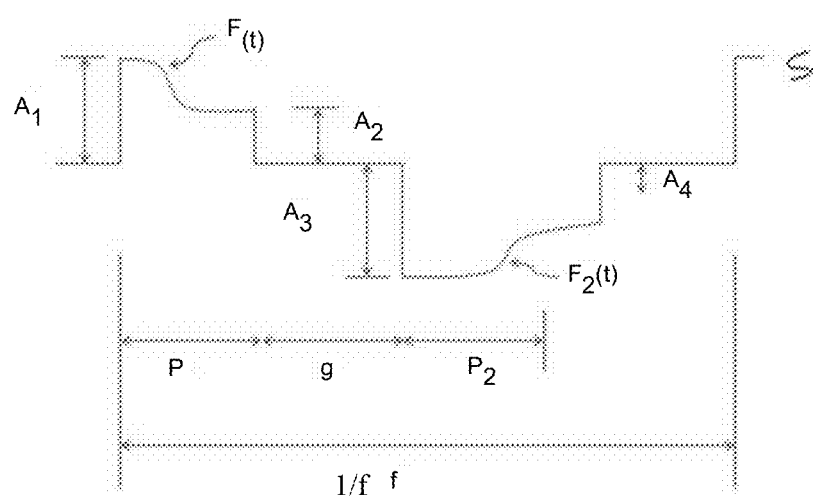
FIG. 12 illustrates a set of stimulus parameters which may be controlled in accordance with the present invention.

The present embodiment thus permits a considerably more generalised definition of the stimulus, as shown in FIG. 12. In this embodiment, parameters which are varied within the parameter search space include:

| | |
|---|---|
| Amplitude | $A_1, A_2, A_3, A_4$ which are the amplitudes of the various peaks. |
| Pulse period | $P_1, P_2$ the duration of the pulses. |
| Interpulse gap | g the gap between the first pulse and the second pulse. |
| Pulse function | $F_1(t)$ and $F_2(t)$ define the shape of each phase |
| Frequency | f determines the repetition rate for the stimulus |

For example, a pure sinusoidal response can be generated with f(t) as a sin function g=0, A2=A3=0. A conventional square biphasic pulse has a parameter set $F_1(t)=-F_2(t)$ =A1=A2=−A3=−A4.

Figure 13:
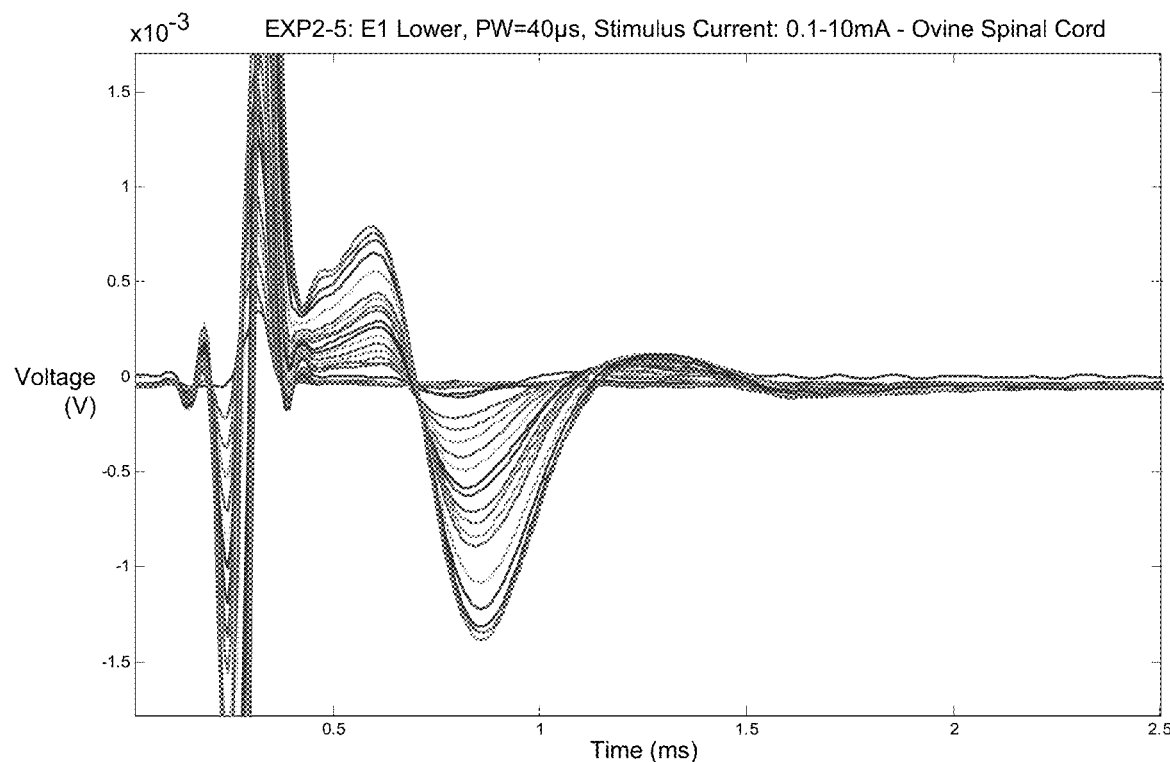
FIG. 13 illustrates ovine compound action potentials resulting from successively applied stimuli of varying amplitudes, in order to ascertain suitable threshold and comfort levels.

FIG. 13 illustrates measured ovine compound action potentials, which arose in response to successively applied stimuli of varying amplitudes, in order to ascertain suitable threshold and comfort levels. The stimulus pulse width was 40 μs. FIG. 13 illustrates that stimulus pulse amplitude can be progressively varied in order to determine a stimulus amplitude at which the greatest fast response is evoked, with the least slow response.

By iteratively refining the stimulus parameters and applying differing stimuli under control of a suitable search algorithm e.g. a genetic algorithm, the stimulus parameter search space can be effectively and swiftly explored to identify a specific set of values for the stimulus parameters which best generate a desired evoked response. There are several parameters that are useful to optimise for the individual. The total charge delivered per stimulus pulse determines the power consumption of the device and hence the time between recharges for a rechargeable device or the lifetime of the device for a non-rechargeable device. The pulse parameters, duration of the inter-phase gap etc, can be varied and the combination which delivers the desired evoked response for the minimum delivered charge can be determined by application of a suitable search technique.

The present invention may further provide for partly or completely automated device fitting. The amplitude of the evoked response provides a measure of the recruitment of the fibres being stimulated. The greater the stimulus, the more recruitment and the larger the evoked response. A plot of the compound action potentials measured in a sheep spine for a number of stimulus amplitudes is shown in FIG. 13. The peak height varies with the amplitude of the applied stimulus in a consistent (i.e. monotonically increasing) way.

Figure 14:
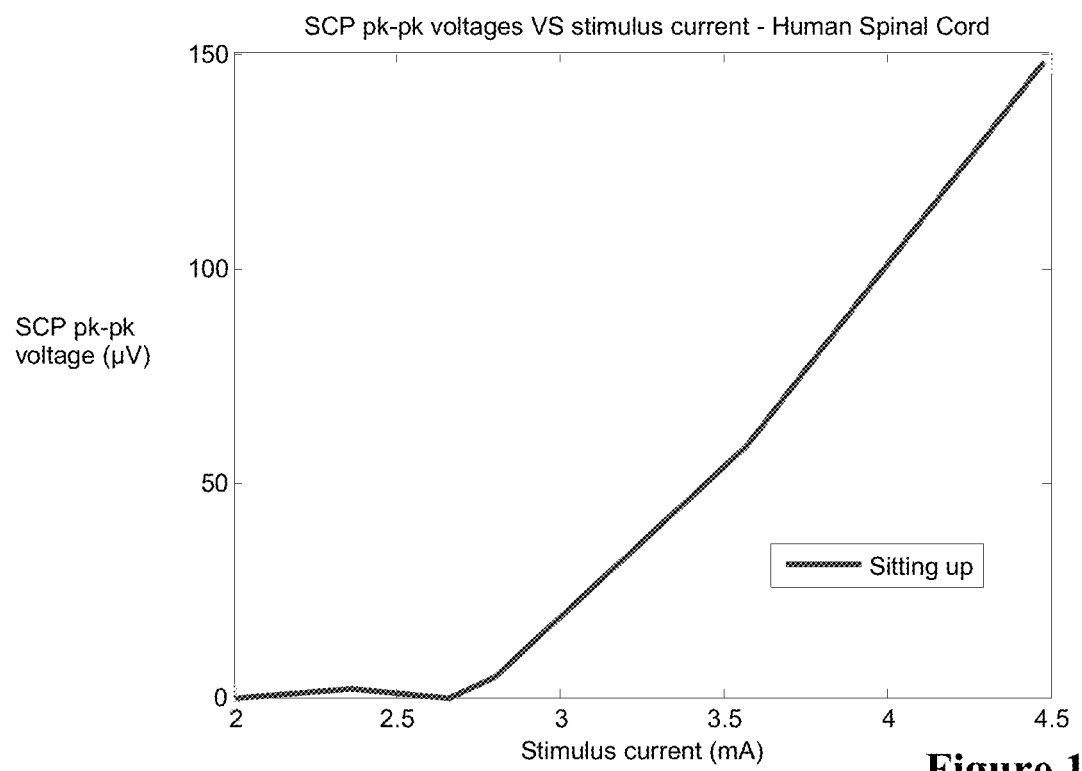
FIG. 14 plots measured spinal cord potential (SCP) amplitude arising from biphasic stimuli of width 120 μs, each stimulus having a current level in the range 0-4.5 mA, as measured in a human subject in a sitting posture.

FIG. 14 plots measured spinal cord potential (SCP) amplitude arising from biphasic stimuli of width 120 μs, each stimulus having a current level in the range 0-4.5 mA, as measured in a human subject in a sitting posture. At some amplitude the patient experiences a sensation derived from the stimulus (at a current of 2.75 mA in FIG. 14). The perception threshold corresponds to the appearance of an evoked response.

There are a number of factors which can influence the amplitude of the response generated by a fixed set of stimulation parameters.

The evoked response for the Aβ fibres can be used in a number of ways during the implantation and subsequent programming of the device. These include:
1. Determining the optimal combination of electrodes to generate the desired therapeutic effect;
2. Selection of the stimulus parameters to generate the desired therapeutic effect;
3. Continuous adjustment of the stimulus parameters to remove variations in recruitment induced by movement, or relative movement of the spinal cord with respect to the electrode position; and
4. Minimisation of stimulation side effects Very often during the assessment of patient suitability for spinal cord stimulation, a trial period is undertaken during which an electrode is temporarily implanted in the epidural space above the spinal cord. The CAP measures of the present invention can be recorded during this implantation and may provide sufficient diagnostic indicator of neurophysiological response to warrant the surgeon performing an implant of the full system.

Figure 15:
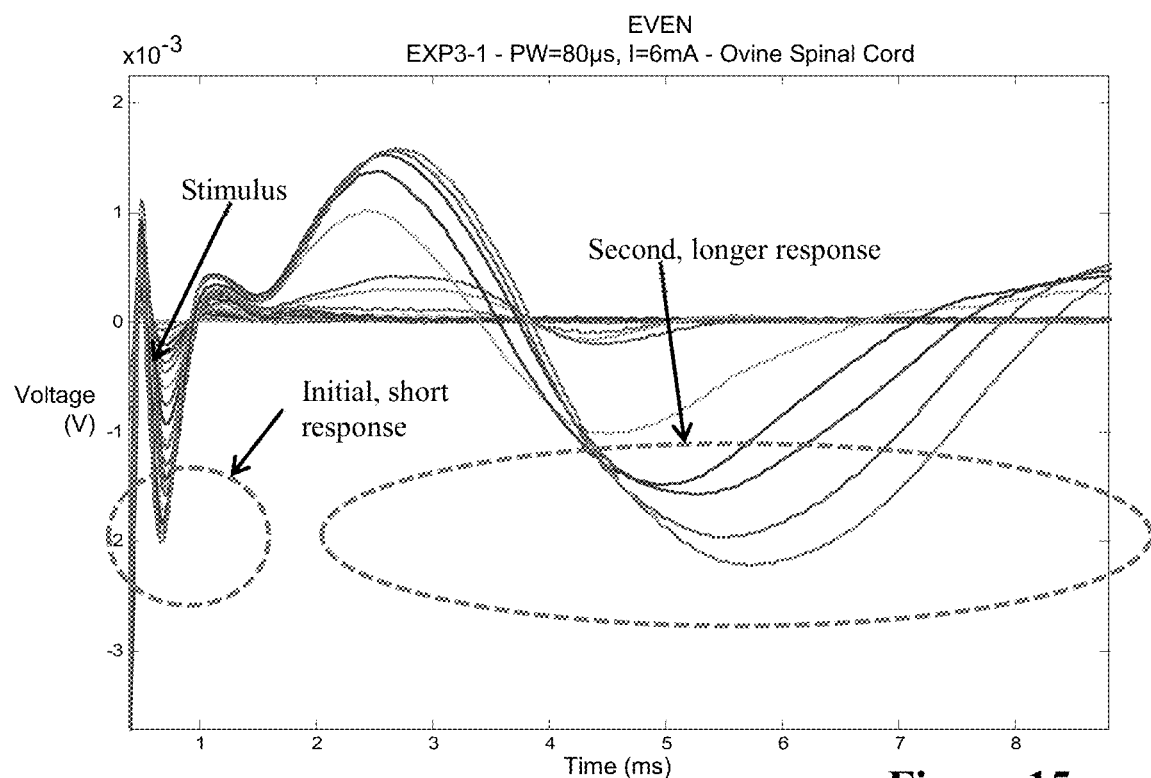
FIG. 15 illustrates the two major response types in an evoked SCP.

The evoked response recorded from the epidural space in the spinal cord varies with the stimulus amplitude and has two components at high amplitudes. It consists of an immediate response (short duration characteristic of the response from fibres with a high conduction velocity), followed by a response with a much longer time scale. The shorter response is characteristic of the recruitment of Aβ fibres in the dorsal column. The response which occurs at longer time scales involves motor system neural responses, EMG, etc. These signal features are shown in FIG. 15.

The normal clinical procedure for adjustment of spinal cord stimulation parameters involves adjustment of pulse width, current and rate to place an induced paraesthesia over the site of pain. There is an upper limit to the intensity of the stimulation, beyond which the patient will not accept further increases, referred to as the dose limit. For some patients this point also corresponds to the point where effective paraesthesia is present and there is good pain relief, however for some, the side effect of the stimulation is intolerable for the patient. Overstimulation of Aβ fibres is also unpleasant for the recipient and unfortunately results in poor efficacy because, although good coverage is obtained, the patient cannot take benefit from the treatment because the side effects are too severe.

The fibre types that are responding at the dose limit have been assessed from patient feedback of the sensations induced. Selected results include:
- 56% of patients reported the sensations which are typical of Aβ responses.
- 15% reported Aδ typical sensations.
- 6% reported C fibre responses.
- 21% reported sensations corresponding to motor muscle spinal responses.

The Aβ fibres are large in diameter (13-20 μm) and much larger than Aδ fibres (1-5 μm) and C fibres (0.2-1.5 μm). The C fibres have the slowest conduction velocity 0.5 to 2.0 m·s$^{-1}$ whereas Aδ fibres have conduction velocity of 3-30 m·s$^{-1}$.

Considering the propagation velocity of recruited Aδ fibres ascending the spinal cord is 15 m·s$^{-1}$, and a typical distance of a spinal cord electrode array is 7 cm long, the propagation delay from one end of the electrode array to the other is 4.6 ms.

Figure 16:
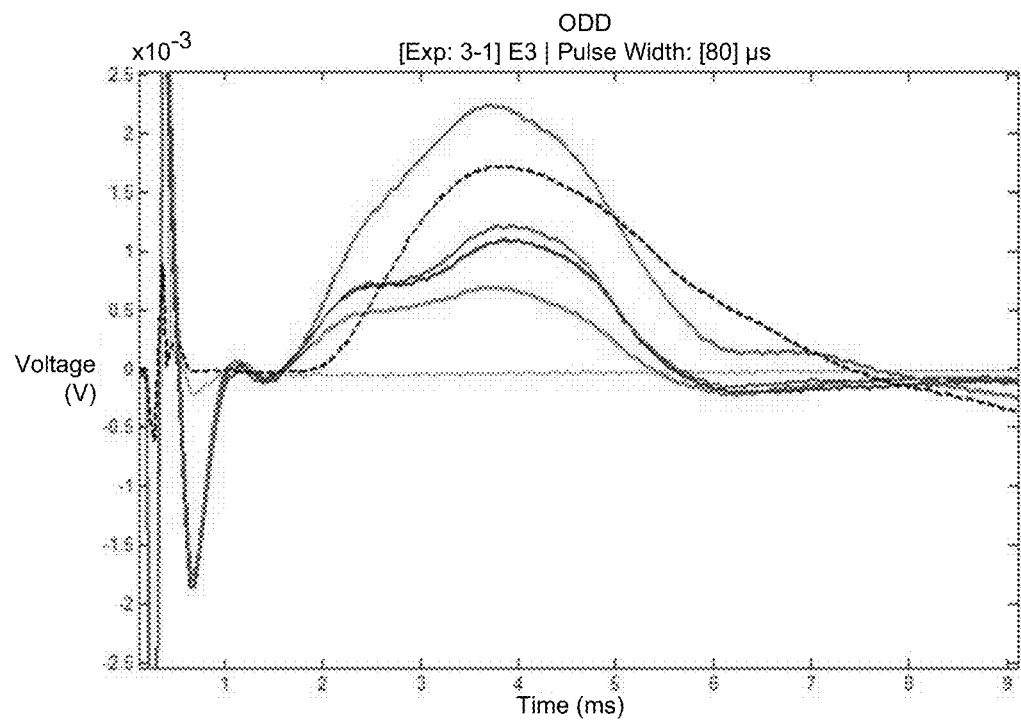
FIG. 16 illustrates measured ovine evoked responses demonstrating fast and slow responses, together with an electromyogram (EMG) trace recorded from an electrode implanted in the corresponding muscle.

FIG. 16 illustrates the evoked response in a sheep spinal cord, demonstrating fast and slow responses. The black dotted line is an electromyogram (EMG) trace recorded from an electrode implanted in the corresponding muscle. The Aβ activity is present in the 0 to 1.5 ms time window. Above a threshold stimulation current level, a slow response is observed 2 ms after stimulation. The slow response is the result of the activation of other neural elements. Activation of the Aδ fibres results in activation of the spinal reflex loop (nociceptive reflex) and can cause muscle contractions. Direct activation of motor neurons also will cause motor responses. Observation of the slow responses in animal experiments was accompanied by the observation of muscle twitching, while observation of the slow response in humans is observed only at uncomfortable stimulation levels.

The present embodiment thus recognises that evoked response measurements such as those of FIG. 15 can be used to determine the allowable dynamic range of stimulation which is available to the patient. In this embodiment, the presence of the slow response is automatically detected by the implanted device, by looking for an evoked response which has a peak from around 3 to 4 ms after the start of stimulation. The slow response is an indicator of the recruitment of fibre classes other than the target Aβ fibres and is accompanied by side effects which are undesirable. The dynamic range available to the patient can be determined by using the onset of a slow response as an indication of an upper limit to the stimulation settings. The slow response can be brought on and measured either during normal use of the device or under general anaesthesia, by adjusting the stimulus level until the slow response characteristic emerges in the measured neural response, indicating that the comfort threshold has been reached. This procedure can be conducted on each electrode of the array, various combinations of electrodes, and in a number of different postures of the patient. A maximum safe stimulation level may then be set in the patient's controller for each electrode.

An alternative measure of the patient's posture (e.g angle detection via a triaxial accelerometer) may be used to select the slow response threshold. Alternatively, an algorithm may be implemented in the implant which simply looks for the presence of a slow response and reduces the output of the stimulator should a slow response be detected.

Another embodiment provides for measurement of a stimulation threshold and creation of a percept body map. The stimulation threshold for neural recruitment can be determined from the peak to peak amplitudes of the fast response. It corresponds to the minimum stimulation level required to produce a psycho-physical sensation. One difficulty faced in programming any neuromodulation system is to determine the locus of stimulation on a perceptual body map. This is because, in existing systems, there is no way to standardise the stimulus such that it produces a constant level of recruitment. Varying the stimulus amplitude has an effect on both the locus of the perceived stimulation and on the area covered. Stimulating at fixed point above threshold (n·$T_e$) for the Aβ fibres allows stimulation at fixed level of recruitment. An accurate body map relating percept with electrode stimulation location can be determined by stimulating each electrode in turn and asking the patient to locate the locus of perception on a graphical body map. The thresholds can be determined for single electrodes as stimulating sites, or for two electrodes used in parallel as a single site, or any other applicable combination of electrodes.

A body map based on threshold or other constant recruitment condition is a useful reference for device control, as it provides a method to select electrodes to achieve the desired level of coverage.

Currently, the task of a clinician programming such a system is to optimise the pain relief by selecting stimulus parameters and location to achieve coverage, i.e. matching the area of paraesthesia with the area over which the patient experiences pain. The choice between stimulating at one or two locations can have an impact on the power consumption of the system. Mapping the percepts at constant Aβ evoked responses allows the clinician and user to quickly identify electrodes which are aligned with the regions required for pain relief. The differences in percept for different combinations of electrodes provide a guide for lowering power consumption. For example, where two electrodes correspond to the same paraesthesia location, then stimulation on those two together will reduce the power consumption of the device.

Yet another embodiment provides for stimulation below the threshold at which paraesthesia is perceived. There are a number of therapeutic benefits obtainable from spinal cord stimulation. For example spinal cord stimulation has been used to treat chronic peripheral vascular disease, in which the mode of action appears to be stimulation of the sympathetic nervous system. Spinal cord stimulation has also been found to be effective in the treatment of chronic leg ulcers. The control of stimulus parameters is complex in this clinical condition. The clinician is not necessarily aiming to produce a paraesthesia in order to generate clinically therapeutic stimulation of the sympathetic nerves. However, in conventional SCS systems, the only indicator that stimulus parameters are producing neuronal depolarisations is through the patient reporting the presence of a paraesthesia. The present embodiment, using neural response measurements, provides a method to objectively quantify the stimulation threshold and may thus permit effective use of sub-threshold stimuli. Using this threshold and its potential variations due to posture, a stimulus parameter can be selected which is below psychophysical threshold, so that continual excitation can be achieved which is below sensation threshold, and independent of posture.

Figure 17:
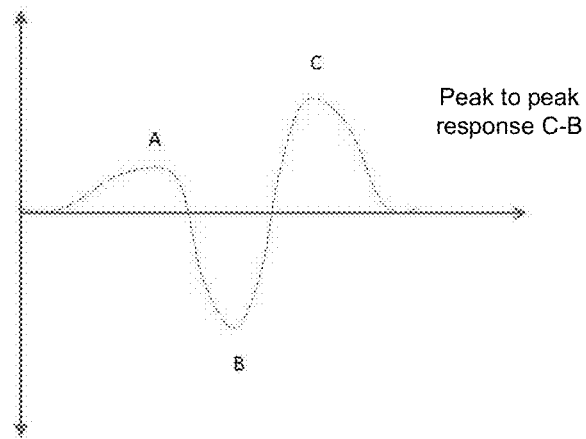
FIG. 17 is a schematic diagram illustrating the measurement of the peak to peak amplitude of the evoked neural response.

In another embodiment, the fast response is measured to set the comfort level without reference to the slow response and indeed possibly without ever causing a slow response. The recorded electrically evoked compound action potential is the sum of a multitude of single fibre evoked responses, and its strength represents the level of recruitment of the fibres (i.e. the size of the signal is proportional to the number of fibres responding to the stimulus). A convenient way to represent this is to measure the peak to peak amplitude of the response (C-B in FIG. 17).

Figure 18:
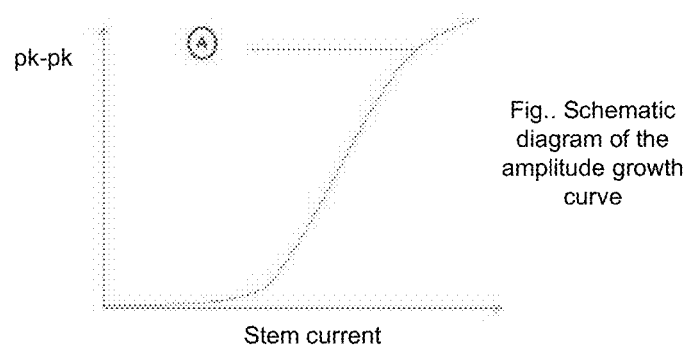
FIG. 18 is a schematic diagram of the neural response amplitude growth curve relative to stimulus current.

The amplitude growth curve for the peak to peak response is readily obtained by measuring the responses at different stimulus parameters (pulse width and current level). The charge on the electrode generates equivalent responses independent of the pulse width. The fast response amplitude growth curve, as illustrated in FIG. 18, can be used to set the comfort level (the level beyond which unwanted side effect stimuli would result), simply by inspection of the growth curve. This embodiment may thus avoid the need to deliberately induce a slow response in order to ascertain the comfort threshold. The stimulus needs to be maintained around or below the point A indicated in FIG. 18. Increasing the current above this point results in no further desirable recruitment and it potentially results in a generation of unwanted or unpleasant slow responses. Point A may be estimated from the amplitude measurements by finding an inflection point in the growth curve, or by noting a reducing gradient of the curve, for example.

Electrode to electrode variation in stimulus thresholds may indicate differences in proximity of electrode to the spinal cord, or that the electrode may be adjacent to neural regions of greater sensitivity. The procedure to locate the ideal electrodes for stimulation efficiency is to create an electrode sensitivity map. This is obtained simply by performing a stimulus current sweep on each electrode, while obtaining neural response measurements at each level, so as to obtain the evoked response amplitude vs. stimulus current curve, for all stimulating sites.

Further embodiments of the invention provide for estimation of the spinal cord-to-electrode distance. In order to maintain a constant level of recruitment, it is necessary to estimate the evoked neural response level arising from a particular stimulation. Given that one of the primary factors affecting recruitment efficacy is relative motion between the spinal cord and the electrodes, it is extremely useful to estimate the cord-electrode distance.

In another embodiment for estimating the cord-to-electrode distance, the relationship of the evoked SCP to the stimulation is exploited. For simple stimulation in the linear region of the amplitude growth curve, recruitment varies with the number of fibres for which the activating function (the axial second derivative of voltage) is above threshold. It can be shown that, in a homogeneous volume conductor (HVC), the activating function varies with $1/d^2$. Hence, for a fixed stimulus current in a HVC, the recruitment varies approximately with $1/d^2$. This embodiment also recognises that, in measuring the SCP, two distance-related factors are prominent. Due to the nature of the fibre, having discrete nodes of Ranvier easily modelled as a line of point current sources, the SCP amplitude in a HVC varies with $1/d^2$ (as well as with fibre diameter). This means that in the linear region of the amplitude growth curve, the combined effect of recruitment sensitivity to d and measurement sensitivity to d causes the measured SCP amplitude to approximately vary with $current*1/d^2*1/d^2$, or $current/d^4$. Based on this recognition, this embodiment therefore applies an algorithm which uses probe stimuli in the linear range (between threshold and onset of saturation), to estimate the cord distance relative to some calibration value. Hence, the recruitment can be estimated for a particular stimulus, relative to some calibration point.

In another embodiment of the invention lateral movement of an electrode is monitored and estimated. This embodiment recognises that anecdotal data from sheep experiments, as well as a consideration of spinal cord anatomy, suggests that as the epidural stimulation site shifts laterally from the midline, the chance of eliciting motor reflexes and other responses of the motor neurons increases. For a given stimulus intensity, if the slow responses appear or become larger than previously, this is an indicator that lateral movement of the electrode has occurred. This scenario may lead to undesired sensation and may need to be rectified. In such embodiments a paddle electrode may be used, comprising multiple columns of electrodes, and then the selection of stimulation electrodes may be changed such that the new stimulus electrodes are medial of the previous off-centre stimulating electrodes. If a single "percutaneous" electrode array is used, the stimulus intensity may be reduced to avoid the undesired sensation produced, or again the stimulus location may be shifted.

Embodiments of the invention may be applied only occasionally, for example only in a clinical setting. Alternatively, automated neural response measurements in accordance with the various embodiments of the invention may be used regularly, or even substantially continuously to adjust the system in real time.

Yet another embodiment of the invention may obtain measures of both the neural response and also electrode impedance as measures of activity for adjustment of the system. The evoked response measurements are sensitive to the distance between the excited neural tissue and the sense electrode. Variations in the position of the electrode affect both the level of recruitment and also the strength of the measured evoked response due to the losses of the electric field propagating in the medium. The variation in the evoked response which is induced by relative movement of the electrode and spinal cord can be used to detect activity and movement of the recipient.

Many recipients of spinal neuromodulators report discomfort or changes in modulation with movement. The evoked potential change could be used to control the stimulus current in a "tight" feedback loop or in a "loose" feedback loop, in order to avoid the stimulus from causing discomfort when the user moves or changes posture. In a loose feedback loop, the evoked response could be used to control the stimulus between say two values, a first setting used for ambulatory periods or periods of activity, and a second setting used for periods with relatively stable evoked response measures. A useful example may be the detection of periods of sleep (relatively low movement) where it would be desirable to turn down the amount of stimulation to conserve battery life during periods of rest. Alternatively, during periods of high activity it may be preferable for the implantee to receive a lower therapeutic (or no therapeutic stimulation) to lower the likelihood of unwanted undesirable stimulation.

In this embodiment, changes in movement are detected and the pattern of these changes is used to control device parameters. In addition to adjusting the stimulus level, this embodiment adjusts other device parameters which have an impact on the operation of the system. Noting that continuous recording of the evoked potential consumes additional electrical power, this embodiment further controls the rate at which measurements are obtained in response to the level of activity. The level of implantee activity may also be logged by the system and used as a measure of the performance of the system in achieving pain relief.

Figure 19:
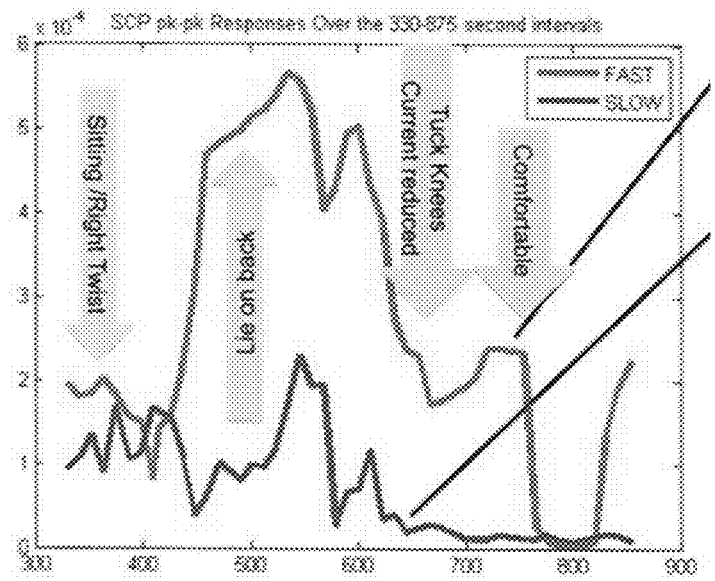
FIG. 19 plots the amplitude of the "fast" and "slow" responses in a human subject while performing postural manipulations.

In embodiments addressing postural changes, a further issue arises in that gross posture alone (as might be measured by an implanted accelerometer) may not sufficiently indicate the appropriate parameters. FIG. 19 provides plots of the amplitude of the "fast" and "slow" responses in a human subject while performing postural manipulations. The posture or relative position of the stimulator gives information about the position of the stimulator. However, in the "fast" curve of FIG. 19 the stimulation efficiency changed when the patient was lying on their back and asked to bring their knees to their chest. Although the stimulation efficiency and patient's perception change significantly, an implanted accelerometer would not have been able to sense these postural changes because the device remains at the same orientation. In contrast, neural response measurements can be used to greatly improve the effectiveness of neurostimulator adjustment when combined with accelerometer measurements of posture. Simultaneously recording neural responses and measuring posture with an accelerometer can be used in an automated process to determine the appropriate parameters for the neurostimulator for a wide range of postures. Notably, such simultaneous recording does not necessarily require implantation of a device equipped with neural response recording capabilities, as it can be performed during the trial stimulation phase when patients have been implanted with an externalised lead.

In such embodiments utilising simultaneous neural response measurements and accelerometer posture measurements, determining the patient parameters comprises:
1. the neural response measurement system is used to record responses under an initially programmed set of conditions.
2. The patient changes posture and the posture is measured via accelerometer and responses recorded at the new posture.
3. Adjustments are made to the stimulus parameters based on the evoked response measurements. The adjustments are made to bring the neural response measure equal to the first neural response measure, preferably accounting for varying measurement sensitivity arising from a changed electrode-to-fibre distance d. Note that the adjustments can be done automatically in a feedback loop.
4. A table of program parameters versus posture parameters is updated with new posture data and program data determined from the neural response.

The process outlined can use any or all of the feedback techniques described herein to adjust the stimulation parameters automatically. In this way programming of the device for different posture settings is simply a matter of setting up the process as described and asking the patient to vary their posture. This could be done over days, for example during the trial stimulation period, improving data quality. An indicator could be provided to give feedback to the patient on the percentage of possible posture variations as determined by the range of the measurement device.

Another advantage of the system as described is the ability to identify postures for which there are ambiguous stimulation parameters; for example, supine with straight legs versus supine with knees to chest. Continuous recording of both posture and feedback parameters based on neural response measurements may allow identification of posture values for which there are two or more different stimulation parameters. If used without neural response measurements, the patient parameter set chosen from an ambiguous parameter set could be the set corresponding to the lowest stimulation current, thus preventing unwanted side effects.

Neural response measurements conducted during a trial stimulation period may be used to create a table of parameters for use with accelerometer-based implants. Neural response measurements can also be used continuously with accelerometer-based measurement. An accelerometer or simple passive movement detection could be used as an indicator of activity. Neural response measurements consume power and so the rate at which they are obtained will have an impact on the battery life of the system. It is highly desirable to manage the rate of measurement (and hence the power consumption). An accelerometer or passive movement detector could be used to detect movement of any type, in response to which the neural response measurement sample rate may be adjusted up or down, so that the response is optimally adjusted with the minimum number of neural response samples acquired.

Employing neural response measurement in a neuromodulation system leads to a variety of available mechanisms for improving the therapeutic outcome of SCS implantees. Discussed below are various control algorithms based on neural response feedback signals. It should be noted that all of these feedback mechanisms may be enabled only when movement is detected, since this is when the stimulus needs to be updated to optimise the pain relief. Enabling feedback control only when movement is detected may also lower the overall power consumption of the implant. Detection of movement may be achieved in a number of ways, including: monitoring via ball-in-tube type detectors, accelerometers, gyroscopes, etc.

Figure 20:
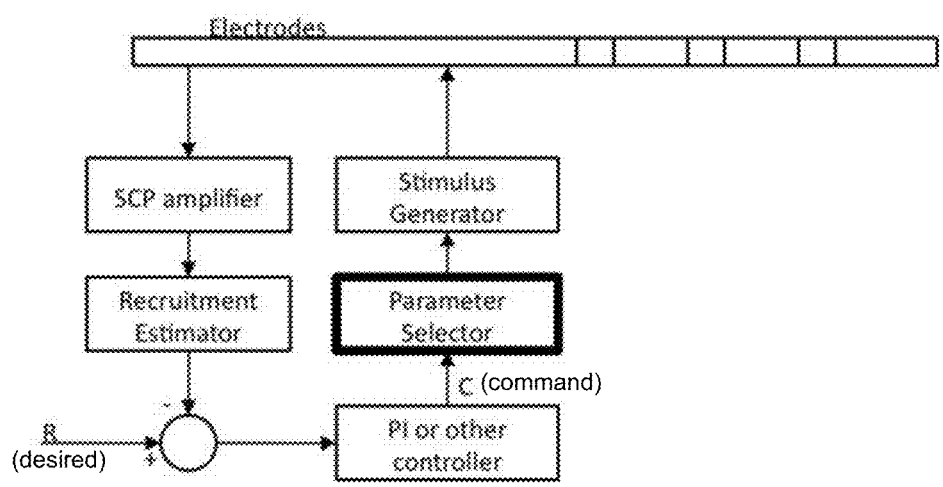
FIG. 20 is a schematic of a feedback controller to effect stimulus control in response to recruitment of neurons.

In order to maintain a constant level of analgesia, it is desirable to recruit enough of the appropriate dorsal column fibres, while avoiding recruitment at levels or in areas associated with side effects. Control of recruitment can be achieved by varying any one of several parameters, such as current or pulse-width. However, when modulating a single parameter, patient discomfort can limit the range of conditions under which recruitment can be held constant. For example, as current increases, fibres lateral to the electrode are more likely to be recruited. Thus, instead of controlling one parameter at a time, it is possible to control several. The choice of parameters is made to minimise discomfort and stimulation energy for any desired stimulation command (up to some programmed limit). FIG. 20 is a schematic of such a feedback controller based on recruitment of neurons.

The simplest implementation is a piecewise specification of stimulation parameters from the command. For example, if we specify that the injected charge should be proportional to the command value:

[[FIGURE—PW/I vs. Command]]

The Command generated is a value which is proportional to the error in the recorded response (ie the difference between the set point and the measured response). The parameter selector can select any parameter to adjust (pulse width, current level, frequency of burst etc). One simple option is to make the charge delivered proportional to the command value which reduces the feedback loop to a simple proportional control loop.

The optimal command-to-stimulus mapping depends on factors including spinal geometry, control loop parameters and desired performance, and the psychophysical requirements of the individual patient. Thus it may be necessary to select between different parameter-selection algorithms depending on external factors, such as movement detection or patient controls.

Figure 21:
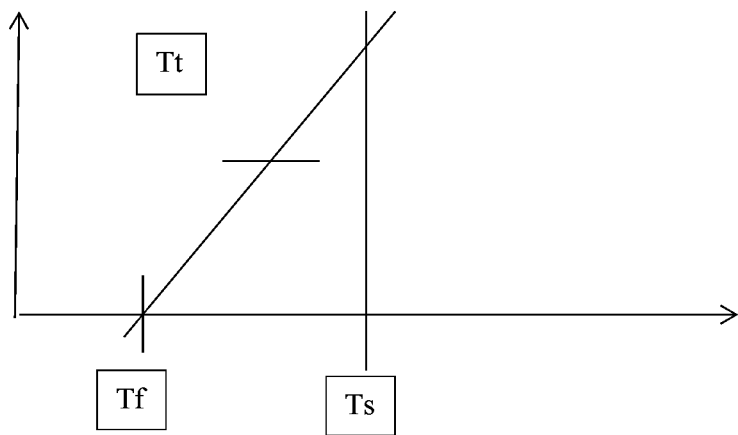
FIG. 21 is a plot of a linear approximation of the SCP growth curve (evoked response amplitude vs. stimulus current), indicating the relationship between various threshold levels.

FIG. 21 is a plot of the SCP growth curve (amplitude vs current), indicating the relationship between various threshold levels: Tf, the threshold for fast response; Ts, the threshold for slow response; and Tt, the threshold for therapeutic response. For automated feedback control, the therapeutic stimulus level is initially set at some point between Tf and Ts. For the initial setting an initial ratio is determined which places Tt between Tf and Ts.

$$Tt-Tf=Rt$$

$$Tf-Ts$$

Then for any subsequent stimuli $$Tt=Ri*(Ts-Tf)+Tf$$

The stimulus which is used to probe the slow response presence or absence is output at frequency which is not annoying to the recipient. The fast (<2 ms) response recorded is due to activation of Aβ fibres in the spinal cord, and the slow response observed accompanies unwanted, uncomfortable or undesirable stimulation (e.g. muscle fibre activation). Thus, the stimulus level should ideally be set between the fast response threshold value (Tf in FIG. 21) and the value at which an unwanted response is evoked.

An algorithm can be defined which is based on the presence or absence of Aβ and slow responses, as follows:
1. A stimulus Sp (=Tf+ΔTs) targeted to be less than the therapeutic stimulus but greater than threshold Tf is used to evoke a response.
   a. If a response is detected in <2.0 ms then do nothing else.
   b. If no response is detected, increment the threshold Tf by an increment ΔTs
2. A stimulus SL (=Ts−ΔTs) targeted to be greater than the therapeutic stimulus but less than that required to elicit a slow response is output
   a. If a slow response is detected, decrement the threshold Ts by ΔTs
   b. If a slow response is not detected, then do nothing.
3. The therapy setting is calculated as a ratio of the difference between the thresholds Tf and Ts.

Embodiments of the present invention may further give an estimation of constant neural recruitment. The electrically evoked compound action potential is a measure of the level of excitation of nerve tissue being excited. The ECAP is the result of the summation of single fibre action potentials from a large number of fibres. The ECAP magnitude depends on the number of fibres and their distance from the sensing electrode. Fibres which are far away from the sense electrode will contribute less to the ECAP due to the strength of the coupling between the sense electrode and the fibre.

Neuromodulation is used to describe the electrical stimulation of tissue in order to produce a therapeutic effect. Passing a current through the tissue and generating action potentials to produce the therapeutic outcome. The number and strength of action potentials in response to the current is not always proportional to current and depends on a number of factors:
   The refractory period of the neurons in the nerve
   The temperature
   The distance from the electrode to the nerve There can be large shifts in the level of recruitment with changes in separation between electrode and tissue, indeed such shifts can take stimulation parameters from sub threshold to above the therapeutic benefit range. This occurs frequently with spinal cord stimulators where an electrode is implanted in the epidural space and the stimulation target is near the dorsal horn of the spinal cord. The separation between the electrode and the target tissue varies with changes in posture. To address this, embodiments of the present invention may measure the strength of the evoked response and use this as the feedback point for control of the stimulus levels. The measured ECAP potential is proportional to the level of neural recruitment and a scaling factor which relates to the separation (and intervening tissue properties) of the sense electrode from the neural elements. In order to generate a target value in order to perform the feedback control, the variation of the signal due to the separation from the electrode must be removed.

The present invention presents a number of methods by which to extract the level of recruitment of the underlying tissue, independent of the separation of the sense electrode. The evoked response recorded for the Aβ fibres from the spinal cord is illustrated in FIG. 14. The amplitude of the response can be characterized by the P2-N1 peak, the N1 peak alone or by the P2 peak alone.

Figure 22A:
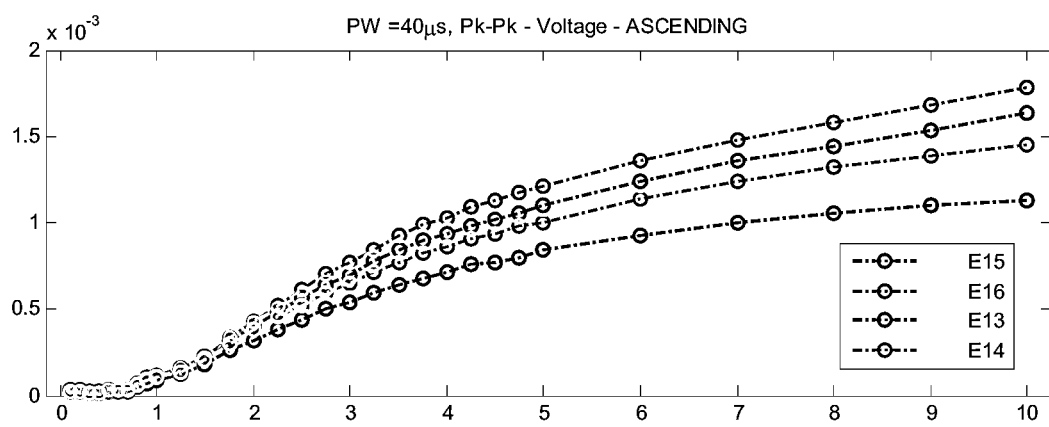
FIGS. 22a and 22b respectively plot the ascending and descending evoked CAP N1-P2 amplitudes each measured on four sense electrodes, recorded in sheep with biphasic 40 us pulse widths
Figure 22B:
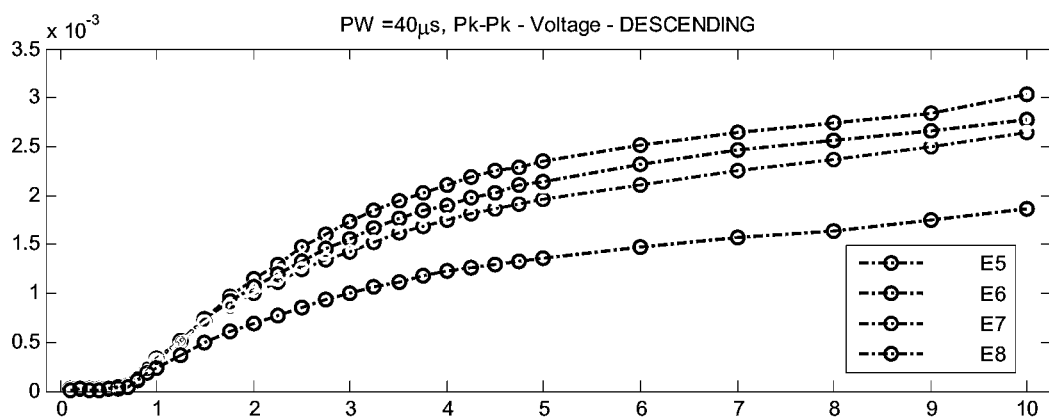

A first embodiment for estimating recruitment in the presence of varying electrode-to-fibre distance d, is based on relative amplitudes found in measurements at two electrodes. The amplitude of the evoked response varies with the applied charge and the response can be measured on a number of different electrodes distant from the electrode where the stimulus is applied. The responses measured in the sheep spinal cord are shown in FIG. 16, for responses in the ascending direction (i.e. for electrodes positioned away from the stimulating electrode along the midline of the spinal cord). FIG. 22a displays the variation in evoked SCP amplitude with varying stimulus current, on four separate electrodes in the ascending direction, while FIG. 22b showing the equivalent in the descending direction. In particular, FIG. 22 shows ascending and descending evoked CAP N1-P2 amplitudes, recorded in sheep in response to biphasic 40 μs stimulus pulse widths.

The amplitude of the responses for electrodes which are more distant from the stimulus site do not increase as markedly with the stimulus current as the electrodes closer to the stimulus site. The distant electrodes are measuring the propagation of the action potential ascending (or descending the spinal cord) and aren't subject to any localized recruitment phenomena. At a given stimulus level above a critical value $A_{sat}$ the number of fibres close to the sense electrode which can be recorded are all recruited and increasing stimulation no longer causes an increase in the amplitude of the response.

Figure 23:
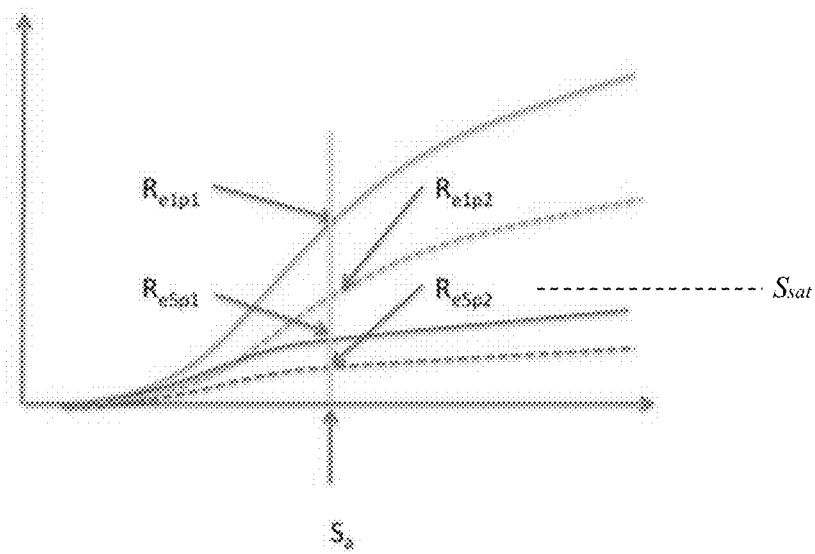
FIG. 23 illustrates respective SCP amplitude response curves, for two sense electrodes which are spaced apart along the spinal cord, and which are at different distances away from the spinal cord.

The different sensitivities of the different regions of measurement can be used to estimate the target value for feedback loop control. Consider the responses at two different positions of the electrode relative to the stimulated tissue, in this case the spinal cord. The amplitude response curve in position 1 labelled p1 in FIG. 23 for electrode 1 and electrode 5 (sub e1 and e5) are illustrated. For an alternative position p2 the responses are scaled by the effect of the change in distance from the electrode. Less tissue is recruited and less evoked response is measured. The amplitude response of the distant electrodes is only weakly dependent above a saturation level $S_{sat}$ of stimulation on changes to the stimulus amplitude. That is, $S_{sat}$ is an amplitude which is asymptotically approached by the response as seen by electrodes distant from the stimulus.

If a completely flat response above $S_{sat}$ is assumed, then the scaling factor due to the shift in distance for this electrode is simply the ratios of the responses at the large electrode separations (Equation 1).

$$R_{e1p2} = (S_s + A_s) R_{e1p1} \qquad \text{Equation 1}$$

The response measured is scaled by a factor $S_s$ which relates to the changed measurement sensitivity, and by a factor $A_s$ which relates to the change in the amplitude due to the change in the recruitment level. For the case when the amplitude at a distant electrode is weakly dependent on the stimulation current, then:

$$R_{e5p2} = (S_s + A_s) R_{e5p1} \qquad \text{Equation 2}$$

and so $$(R_{e1p2}/R_{e1p1}) - (R_{e5p2}/R_{e5p1}) = A_s \qquad \text{Equation 3}$$

Knowing $A_s$ thus permits estimation of actual neural recruitment from the measured response, even in the presence of varying electrode-to-fibre distance d.

A second embodiment for estimating neural recruitment in the presence of varying electrode-to-fibre distance d, is based on a two point method. The evoked response measured on one electrode has an almost linear dependence on the applied current, in the operating region between threshold and saturation and for a given stimulation pulse width. The response changes (independent of pulse width) with applied charge. If we consider two response curves at two different postures P1 and P2, then they will have different amplitude and saturation point, which will depend on the separation of the electrode from the tissue in each respective posture.

For a fixed electrical activity in the spinal cord the effect of moving the sense electrode away will be to scale the response curve by the factor which relates to the separation. The electrical activity however changes because in this case the sense electrode and the stimulating electrode are both moving with respect to the spinal cord. Movement of the stimulating electrode away from the spinal cord has the effect of lowering the resultant induced electrical activity in the spinal cord because of a reduction in the field strength and this has the effect of shifting the threshold.

Figure 24:
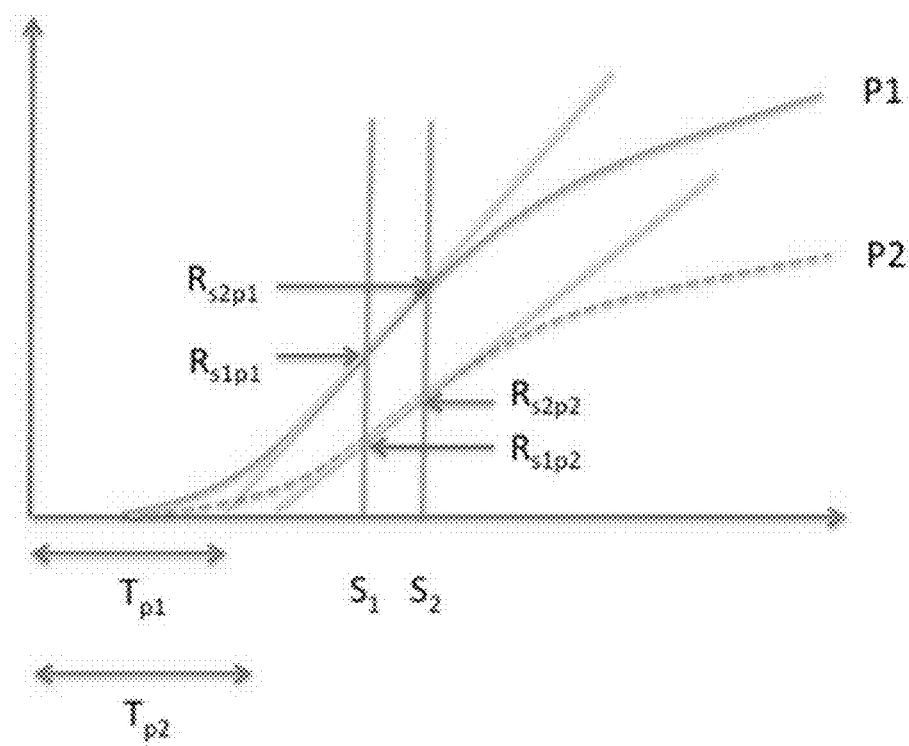
FIG. 24 illustrates theoretical SCP amplitude response curves corresponding to two different postures of the user, in order to illustrate SCP slope determination via a 2-point method.

FIG. 24 shows SCP amplitude response curves for two different postures, indicating slope determination via a 2-point method. The slope and the thresholds of the linear responses can simply be determined from the measurement of the responses at two different current (stimulation) levels in the linear portion of the respective amplitude growth curve. More stimulation levels may be employed to generate more accurate estimates of the slope and the response. For the two different postures P1 and P2 reflected in FIG. 24 the response is measured for two different stimulus intensities S1 and S2, which generate four different responses.

The equation of the respective line is simply:

$$r = R_{s2p1} + ((R_{s1p1} - R_{s2p1})/(S1-S2)) * (S-S2) \quad \text{Equation 4}$$

for P1, and $$r = R_{s2p2} + ((R_{s1p2} - R_{s2p2})/(S1-S2)) * (s-S2) \quad \text{Equation 5}$$

for P2.

The strength of recruitment is not related directly to the response recorded, due to the influence of the displacement upon the sense electrode. However, the intercept of the line of equation 4 or 5 with the x axis approximates the threshold, i.e. the minimum stimulus at which a neural response arises. The threshold can then be used to establish the stimulus parameter control loop variable to respond to changing d.

$$T_{p1} = R_{s2p1} - ((R_{s1p1} - R_{s2p1})/(S_1 - S_2)) * S_2 \quad \text{Equation 6}$$

The threshold scales with the influence of the change in electric field as a result of the displacement. In order to achieve a constant level of recruitment the threshold estimate determined in this manner can be used to determine the target response signal for the control loop.

Figure 25:
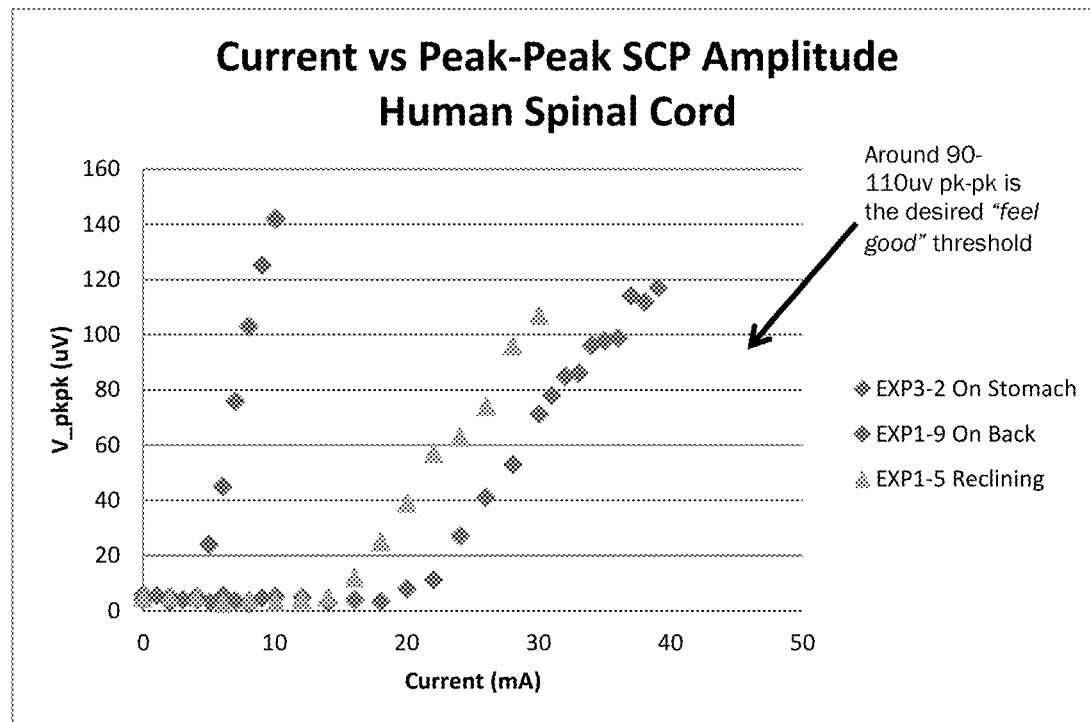
FIG. 25 illustrates three SCP amplitude response curves measured from a human subject in three respective postures.

FIG. 25 shows exemplary data collected from a human subject in three different postures: lying prone, lying supine, and reclining. The peak-to-peak amplitude is plotted against the stimulation current. The threshold values calculated from linear fits to the straight line of the type set out in equations 4 and 5 can be used to estimate the stimulus required to achieve the same level of neural recruitment, independent of the position of the electrode. As can be seen in FIG. 25, the technique of this embodiment of the invention provides strong differentiation between user postures, permitting automated feedback control of changed postures. Moreover, FIG. 25 reveals that if the stimulus was adjusted to give the same amplitude of the measurement of evoked response, the stimulus value would be in error by 20% in the two extremes of the posture.

The stimulus intensity scaled by the threshold value corresponds to a psycho-physical percept of the paraesthesia. For the individual whose data is displayed in FIG. 25, threshold corresponded to sensation on the left leg. The threshold was measured by adjustment of the stimulus intensity and asking the patient to describe the location and strength of the sensation. This task was performed in three different postures, with the patient sitting up, on their back and lying on the stomach, represented in the three rows of Table 1. The first sensation experienced was in the left leg, and the calculated thresholds from linear fits to the lines as per equations 4 and 5 correspond well with the measured thresholds. As the stimulus intensity increased, the range of coverage increased, covering both legs. The stimulus level required to achieve this psycho-physical threshold is different at all the different postures. The stimulation current required to produce an identical psysco-physical response irrespective of the posture can be calculated from the threshold value (for that current posture), multiplied by a scaling factor determined from the measurement at another different posture.

TABLE 1

| Thresholds mA | Leg | Both Legs | Measured | Lower Back | Measured |
|---|---|---|---|---|---|
| 3.9 | 5 | 4.0 | 6 | 6.7 | 10 |
| 14.2 | 12 | 14.8 | 16 | 24.5 | 24 |
| 19.2 | 16 | 20 | | 33 | |

Thus, electrically activated compound action potential can be used to predict the stimulation level required to achieve a constant psychophysical percept.

A further embodiment for estimating neural recruitment even in the presence of varying electrode-to-fibre distance d, is based on peak position within the measured neural response. The recruitment of a nerve fibre in an electric field is a probabilistic event. Increasing the electric field strength increases the probability of firing. The higher the field strength the more likely any one nerve will fire and the firing of those nerves will become more and more synchronised. The result of the synchronisation is a sharpening of the peak and shift of the peak closer toward the stimulus time. The recorded peak will have a shorter interval from the onset of stimulus to peak height for higher stimulation intensities. Peak position thus presents a signal feature which may be analysed to assess actual recruitment.

A further embodiment for estimating neural recruitment even in the presence of varying electrode-to-fibre distance d, is based on spectral characteristics of the measured neural response. As the distance d changes, the fibre-to-electrode transimpedance function shape changes, as can be understood by reference to the cable model of a myelinated axon, for convolutional modelling. A myelinated axon consists of a tube formed of active axonal membrane, sheathed in a layer of insulating myelin. This myelin sheath is interrupted at regular intervals, exposing the membrane to the external medium. These gaps, the nodes of Ranvier, occur at intervals of approximately 100 times the axon diameter, across many types of myelinated nerve. This physical structure permits analysis with a discrete cable model; the inside of the axon is assumed to be a homogeneous conductor, while the membrane ion channel dynamics can be modelled as a nonlinear, time-variant conductance across the membrane at the nodes of Ranvier The change in shape of the fibre-to-electrode transimpedance function in response to a change in d has the effect of smearing the SCP out in time with increased distance, which also reduces its peak-to-peak amplitude. This time-domain change can be measured independently of amplitude, to obtain a direct estimate of distance variation. The propagating action potential in a single fibre is related to a corresponding action current through the fibre's cell membrane. After the AP is initiated in the fibre, the change in potential at one point in the fibre causes ion channels in the nearby membrane to open and close, permitting the flow of a current which then changes the potential further along. In this way, the action current/potential propagate continuously along unmyelinated fibres (such as C fibres), and jump from node to node along myelinated fibres (such as A and A fibres). Action potentials propagating along many nerves in a bundle give rise to a measurable compound action potential (CAP). This measured potential is the sum of the effects of the individual action currents along each fibre; a strong current into the fibre is seen at the leading edge of the activation, while an out-ward current follows, as the fibre's membrane recovers. This may be modelled, for each point on the fibre, as experiencing a fixed action current waveform, delayed proportional to the point's distance from the site of initiation. These currents sum into a potential, due to the resistive nature of the tissues and fluids involved, and for simple cases, may be modelled as a simple volume conductor.

In this case, there is a function for the current at any time at any point along the fibre $I(t,x)$; given the current under the activation site $I(t,0)=I_0(t)$ and the speed with which the activation propagates, v, this is given by:

$$I(t,x)=I_0 t-x/v$$

For a linear medium, there is also a transfer function $F(x)$ from the current at any point along the fibre to the induced voltage on the measuring electrode V:

$$V(t)=\Sigma \times F(x)I(t,x)$$

With suitable scaling, it can then be seen that the measured potential from a propagating action current in a single fibre is given by the convolution of $I_0$ with F.

Letting $F'(x)=F(vx)$:

$$V(t)=\Sigma \times F'(x)I_0(t-x)=F'*I_0$$

F in a simple volume conductor has a definition similar to $$F(x)=1/(d^2+x^2)$$

where d is the fibre-electrode distance, and x is the position along the fibre (relative to the electrode).

Due to the convolution equivalence, we can see that F acts as a time-domain filter kernel applied to I; and since the shape, and hence spectral characteristics, change with d, the filter will exhibit different spectral characteristics at different distances. This recognition can be exploited by, for example, picking two frequencies which are prominent in the compound action potential. By examining the ratio of the selected frequencies, changes in electrode-to-cord distance can be measured, regardless of recruitment percentage.

One key benefit of adjusting programming parameters on the basis of neural response measurements is the ability to understand the relative position of the therapeutic stimulus in the amplitude growth curve. There are two distinct tasks required in the adjustment of program parameters for spinal cord stimulation systems and these are:
1) Matching location of paraesthesia to pain location, and
2) Achieving sufficient coverage such that the area of paraesthesia overlaps the area of pain.

Both these need to be achieved without side effects.

Figure 26:
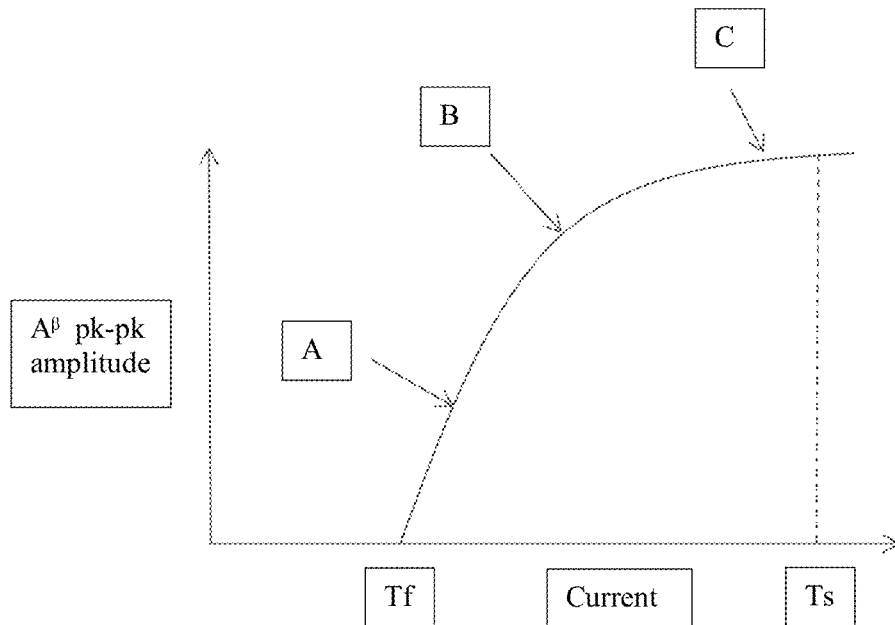
FIG. 26 is an idealised representation of an SCP amplitude growth curve to illustrate salient features.

FIG. 26 is a schematic representation of an SCP amplitude growth curve, with salient features noted. Very often a clinician will find the best electrodes for location (step (1) above) and then wind up the current to achieve the coverage desired (step (2)). In the absence of ERT measures, it is impossible for the clinician to know where the therapeutic setting is with respect to the fast response stimulus threshold (Tf in FIG. 26) and slow response stimulus threshold (Ts).

A situation where the therapeutic level is adjusted to position C in FIG. 26 is undesirable because the stimulus is close to the slow response threshold. The ideal location for the therapeutic stimulus current is at position B as this gives the most sensitive response to stimulus. Adjustments to the stimulus have a greater impact on the peripheral response from the individual. The problem then becomes ensuring that, for a stimulus of a level B, there is sufficient coverage by the paraesthesia to correspond to the area of pain.

An alternative way to address this is by stimulating at alternating locations. The choice to begin to spread the stimulus locations is based on the position of the stimulus current in the amplitude growth curve. A rule set can be developed to make those choices in an automated manner based on the neural response measurements. For instance, stimulation may be applied on alternating electrodes after the current reaches a point B.

Collection of programming data, paraesthesia coverage and neural response measurements can be used to derive a set of rules for an expert system to set up the ideal parameters for the system. Alternating or roving stimuli can be used to extend the coverage of paraesthesia. Alternating stimuli can be used with all stimuli output at the optimal rate (for example 40 Hz).

It will be appreciated by persons skilled in the art that numerous variations and/or modifications may be made to the invention as shown in the specific embodiments without departing from the spirit or scope of the invention as broadly described. For example, embodiments described in the context of spinal cord stimulation may in some cases be applied to other forms of neural stimulation and it is to be understood that such other contexts are within the scope of the present invention. The present embodiments are, therefore, to be considered in all respects as illustrative and not restrictive.

The invention claimed is:

1. A method of suppressing pain by controlling a neural stimulus, the method comprising:
    applying the neural stimulus to a neural pathway of a patient in order to evoke a neural compound action potential on the neural pathway, the stimulus being defined by a stimulus parameter;
    measuring the neural compound action potential evoked by the stimulus,
    deriving from the measured evoked neural compound action potential a feedback variable; and
    completing a feedback loop for applying the neural stimulus by using the feedback variable to adjust the stimulus parameter,
    wherein completing the feedback loop comprises:
    determining an error signal based on a difference between the feedback variable and a set point;
    scaling the error signal by a gain; and
    determining a value for the stimulus parameter based on the scaled error signal.

2. The method of claim 1, wherein the feedback variable is an amplitude measure of the evoked neural compound action potential.

3. The method of claim 1, wherein the stimulus parameter is an amplitude of a stimulus current.

4. The method of claim 1, wherein obtaining the value for the stimulus parameter comprises integrating the scaled error signal to obtain a value for the stimulus parameter.

5. The method of claim 1, wherein obtaining the value for the stimulus parameter comprises adjusting the stimulus parameter by the scaled error signal.

6. An implantable device for suppressing pain by controllably applying a neural stimulus, the implantable device comprising:
- a plurality of electrodes including one or more stimulus electrodes and one or more sense electrodes;
- a stimulus source configured to provide a neural stimulus to be delivered from the one or more stimulus electrodes to a neural pathway of a patient to evoke a neural compound action potential on the neural pathway;
- measurement circuitry for measuring the evoked neural compound action potential sensed at the one or more sense electrodes; and
- a control unit configured to:
    - control the stimulus source to provide the neural stimulus according to a stimulus parameter;
    - measure via the measurement circuitry a neural compound action potential evoked by the stimulus;
    - determine from the measured evoked neural compound action potential a feedback variable; and
    - complete a feedback loop for applying the neural stimulus by using the feedback variable to adjust the stimulus parameter,
- wherein the control unit is configured to complete the feedback loop by:
    - determining an error signal based on a difference between the feedback variable and a set point;
    - scaling the error signal by a gain; and
    - determining a value for the stimulus parameter based on the scaled error signal.

7. The implantable device of claim 6, wherein the feedback variable is an amplitude measure of the evoked neural compound action potential.

8. The implantable device of claim 6, wherein the stimulus parameter is an amplitude of a stimulus current.

9. The implantable device of claim 6, wherein the control unit is configured to obtain the value for the stimulus parameter by integrating the scaled error signal to obtain a value for the stimulus parameter.

10. The implantable device of claim 6, wherein the control unit is configured to obtain the value for the stimulus parameter by adjusting the stimulus parameter by the scaled error signal.

* * * * *